(12) United States Patent
Charizanis et al.

(10) Patent No.: US 10,655,170 B2
(45) Date of Patent: May 19, 2020

(54) COUPLING ADAPTORS TO A TARGET NUCLEIC ACID

(71) Applicant: Takara Bio USA, Inc., Mountain View, CA (US)

(72) Inventors: Konstantinos Charizanis, Mountain View, CA (US); Marta Gonzalez-Hernandez, Mountain View, CA (US); Amanda McNulty, Mountain View, CA (US); Karl Hecker, Mountain View, CA (US); Emmanuel Kamberov, Mountain View, CA (US); John Langmore, Mountain View, CA (US)

(73) Assignee: Takara Bio USA, Inc., Mountain View, CA (US)

( * ) Notice: Subject to any disclaimer, the term of this patent is extended or adjusted under 35 U.S.C. 154(b) by 16 days.

(21) Appl. No.: 15/642,263

(22) Filed: Jul. 5, 2017

(65) Prior Publication Data
US 2018/0010178 A1    Jan. 11, 2018

Related U.S. Application Data

(60) Provisional application No. 62/358,633, filed on Jul. 6, 2016.

(51) Int. Cl.
| | | |
|---|---|---|
| *C12Q 1/68* | (2018.01) | |
| *C12N 15/10* | (2006.01) | |
| *C12Q 1/6855* | (2018.01) | |
| *C12Q 1/6874* | (2018.01) | |
| *C12Q 1/6806* | (2018.01) | |
| *C12N 15/66* | (2006.01) | |

(52) U.S. Cl.
CPC ....... *C12Q 1/6855* (2013.01); *C12N 15/1093* (2013.01); *C12N 15/66* (2013.01); *C12Q 1/6806* (2013.01); *C12Q 1/6874* (2013.01)

(58) Field of Classification Search
None
See application file for complete search history.

(56) References Cited

U.S. PATENT DOCUMENTS

| | | |
|---|---|---|
| 7,309,571 B2 | 12/2007 | Nelson |
| RE44,265 E | 6/2013 | Landegren et al. |
| 8,574,864 B2 | 11/2013 | Vaidyanathan et al. |
| 8,962,253 B2 | 2/2015 | Kazakov et al. |
| 9,023,769 B2 | 5/2015 | Drmanac et al. |
| 9,212,378 B2 | 12/2015 | Choi et al. |
| 2002/0004592 A1 | 1/2002 | Connor et al. |
| 2008/0108804 A1 | 5/2008 | Hayashizaki et al. |
| 2009/0181861 A1* | 7/2009 | Li ........................ C12Q 1/6869 506/16 |
| 2012/0003657 A1* | 1/2012 | Myllykangas ....... C12Q 1/6869 435/6.12 |
| 2012/0164651 A1* | 6/2012 | Kazakov ................ C12Q 1/682 435/6.12 |
| 2013/0157259 A1 | 6/2013 | Choi et al. |
| 2013/0157269 A1 | 6/2013 | Kim et al. |
| 2015/0087556 A1 | 3/2015 | Ambros et al. |
| 2015/0099671 A1 | 4/2015 | Moore et al. |
| 2015/0211046 A1 | 7/2015 | Kazakov et al. |
| 2015/0284716 A1 | 10/2015 | Corey et al. |

FOREIGN PATENT DOCUMENTS

| | | |
|---|---|---|
| EP | 2224016 A1 | 9/2010 |
| EP | 2419537 B1 | 1/2014 |
| WO | WO 2004/070053 A2 | 8/2004 |
| WO | WO 2009/026148 A1 | 2/2009 |

OTHER PUBLICATIONS

Zhang et al.(Genome biology 14.10 (2013): R109; 13 pages) (Year: 2013).*
Zhang 2013 supp (Year: 2013).*
Smith et al. (Nucleic acids research 38.13 (2010): e142-e142; 7 pages) (Year: 2010).*

* cited by examiner

*Primary Examiner* — Tracy Vivlemore
*Assistant Examiner* — Sahana S Kaup
(74) *Attorney, Agent, or Firm* — Kathleen Y. Rao; Bret E. Field; Bozicevic, Field & Francis LLP

(57) ABSTRACT

Methods of coupling adaptors to a target nucleic acid include coupling a first adaptor to a first end of the target nucleic acid to form a coupled first adaptor. A portion of a second adaptor is hybridized to a portion of the coupled first adaptor to form a hybridized second adaptor having a single-stranded 3'-end. The hybridized second adaptor is coupled to a second end of the target nucleic acid to form an adaptor-flanked product having at least a part of the first adaptor coupled to the first end of the target nucleic acid and at least a part of the second adaptor coupled to the second end of the target nucleic acid. These methods can minimize the formation of adaptor-dimers that may be problematic in subsequent complementary nucleic acid strand synthesis, amplification, and sequencing.

26 Claims, 12 Drawing Sheets

Specification includes a Sequence Listing.

COUPLING ADAPTORS TO A TARGET NUCLEIC ACID

CROSS-REFERENCE TO RELATED APPLICATION

Pursuant to 35 U.S.C. § 119 (e), this application claims priority to the filing date of the U.S. Provisional Patent Application Ser. No. 62/358,633, filed Jul. 6, 2016; the disclosure of which application is herein incorporated by reference.

INTRODUCTION

This section provides background information related to the present disclosure which is not necessarily prior art.

Considerable interest resides in reformatting nucleic acids and creating libraries of target nucleic acids for use in various amplification, sequencing, and/or analytical techniques. Such methods can include the addition of adaptors (e.g., synthetic nucleic acids or nucleic acid analogues) to the ends of a target nucleic acid to facilitate manipulation and identification of the target nucleic acid and to aid in subsequent amplification and/or sequencing of the target nucleic acid. For example, adapters that contain one or more primer sequences can be ligated to the ends of a target nucleic acid, where one type of adapter or multiple types of adapters can be used in the ligation reaction. Such methods enable one or more target nucleic acid molecules to be amplified in a single amplification reaction, including, for example, target nucleic acids of known and unknown sequence, as well as multiple target nucleic acids of identical or different sequences. Such reformatted target nucleic acids and/or libraries thereof can be readily subjected to various qualitative and quantitative analyses.

As one example, evaluating nucleic acid expression (e.g., the transcriptome of a cell or population of cells) can be integral to understanding cell development and disease. Various technologies, including sequencing-based approaches, can be used to identify and quantify both coding and noncoding RNAs, including various small RNAs that can play important regulatory roles. Non coding RNAs (ncRNAs) include those classified as small ncRNAs, micro-RNA (miRNA), short interfering RNA (siRNA), and piwi-interacting RNA (piRNA), small nucleolar RNA (snoRNA) and long ncRNAs. The identity of many, if not most, of the ncRNAs in the genome have yet to be discovered and validated for function. Evidence has shown that many of these ncRNAs can play key roles in processes such as cellular differentiation, cell death, and cell metabolism.

In order for small RNAs to be isolated and sequenced, a series of steps including one or more ligation reactions, reverse transcription, and amplification can be used to reformat the target RNA for sequencing on various types of sequencing instruments. An important step in the preparation or reformatting of small RNA for sequencing can be the one or more ligation reactions, where one or more adaptors are attached to one or both ends of the target RNA. Using an enhanced ligation buffer solution and a longer time period of incubation, this portion of the preparation and reformatting of the RNA can be optimized to some extent, thereby providing an increase in the amount of small RNA material being ligated.

However, a considerable drawback in reformatting nucleic acids, such as small RNAs, and the preparation of libraries for sequencing can include the undesirable formation of adapter-dimers (or adaptor-multimers) in the one or more ligation reactions used to attach adaptors to one or both ends of target nucleic acids. Such adaptor-dimers, which may not include a target nucleic acid sequence, can present several issues in subsequent processing steps, including skewing amplification of the resulting nucleic acid library, distorting the representation of individual sequences in the library, and making quantitation of the nucleic acid library difficult. Ways to minimize or prevent the formation of adaptor-dimers could substantially improve the reformatting of nucleic acids and the generation of nucleic acid libraries for sequencing and other analyses.

SUMMARY

The present technology includes systems, processes, articles of manufacture, and compositions that relate to coupling adaptors to a target nucleic acid.

In certain embodiments, a method of coupling adaptors to a target nucleic acid is provided that includes coupling a first adaptor to a first end of the target nucleic acid to form a coupled first adaptor. A portion of a second adaptor is hybridized to a portion of the coupled first adaptor to form a hybridized second adaptor, where the hybridized second adaptor includes a single-stranded 3'-end. The hybridized second adaptor is coupled to a second end of the target nucleic acid to form an adaptor-flanked product, the adaptor-flanked product including at least a part of the first adaptor coupled to the first end of the target nucleic acid and at least a part of the second adaptor coupled to the second end of the target nucleic acid.

In certain embodiments, the hybridized second adaptor can include a bridging oligonucleotide and a ligation oligonucleotide. The bridging oligonucleotide can include the portion of the second adaptor that hybridizes to the portion of the coupled first adaptor to form the hybridized second adaptor and can also include another portion that hybridizes with a portion of the ligation oligonucleotide. The ligation oligonucleotide can include the single-stranded 3'-end of the hybridized second adaptor.

In certain embodiments, the hybridized second adaptor can include at least one cleavable site between the portion of the second adaptor that hybridizes to the portion of the coupled first adaptor and another portion of the second adaptor that includes the single-stranded 3'-end. The at least one cleavable site can be cleaved after coupling the hybridized second adaptor to the second end of the target nucleic acid. The cleaving can result in the portion of the second adaptor that hybridizes to the portion of the coupled first adaptor to include an extendible 3'-end and the another portion of the second adaptor that includes the single stranded 3'-end to be coupled to the second end of the target nucleic acid.

In certain embodiments, the hybridized second adaptor includes a 5' to 5' reverse linker. The 5' to 5' reverse linker can be intermediate to the portion of the second adaptor that hybridizes to the portion of the coupled first adaptor and another portion of the second adaptor that includes the single-stranded 3'-end. The single-stranded 3'-end of the hybridized second adaptor can include a first hydroxyl group and coupling the hybridized second adaptor to the second end of the target nucleic acid can include ligating the single-stranded 3'-end of the hybridized second adaptor including the first hydroxyl group to a 5'-end of the target nucleic acid including a phosphate group. The second adaptor can include another 3' end, where the another 3' end can include a second hydroxyl group. The method can further include extending the another 3' end and synthesizing a complementary nucleic acid strand.

In certain embodiments, a kit for coupling adaptors to a target nucleic acid is provided that can include one or more of the various adaptors described herein. The kit can include a first adaptor and a second adaptor. The first adaptor can include an adenylated 5'-end and a blocked 3'-end. The second adaptor can include a portion configured to hybridize to a portion of the first adaptor, where the second adaptor can include a single-stranded 3'-end when hybridized to the first adaptor. The second adaptor can be configured to hybridize to the first adaptor so that a 5'-end of the first adaptor is double-stranded. The second adaptor can include a blocked 5'-end and the single-stranded 3'-end of the hybridized second adaptor can include a hydroxyl group. The kit can include one or more various enzymes and reagents necessary to practice the various methods and steps described herein. The kit can also include one or more amplification primers, where various amplification primers can have a 3'-end configured to hybridize to at least one of a portion of the first adaptor, a portion of a complement of the first adaptor, a portion of the second adaptor, and a portion of a complement of the second adaptor. The one or more amplification primers can include a barcode.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 5:
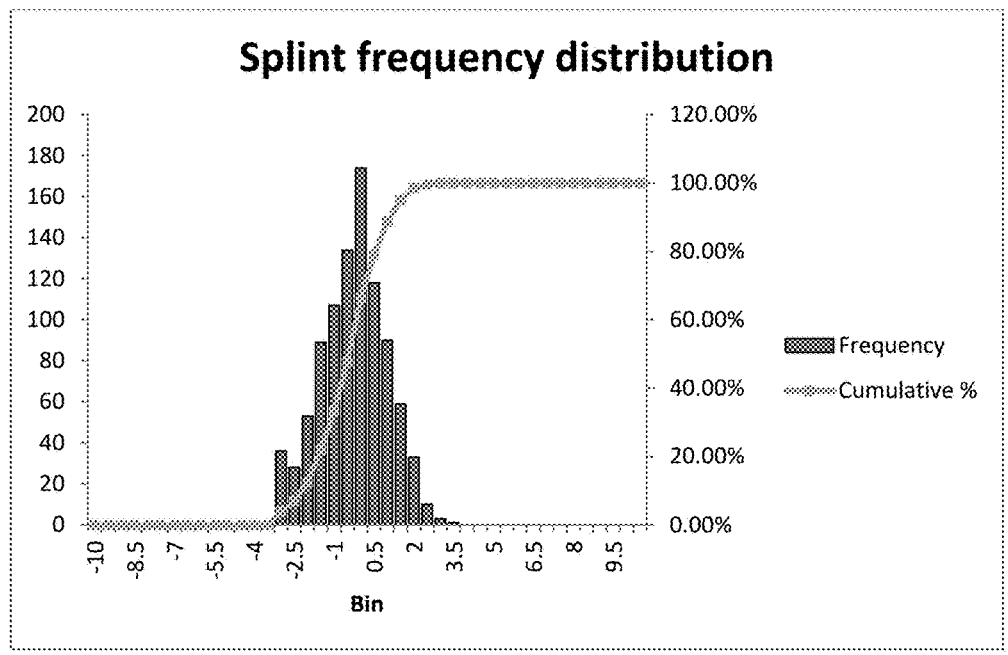

FIG. 5 provides a graphical illustration of results obtained from the experiment described in the working exemplification section, below.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments. Except where otherwise expressly indicated, all numerical quantities in this description are to be understood as modified by the word "about" and all geometric and spatial descriptors are to be understood as modified by the word "substantially" in describing the broadest scope of the technology.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

The present technology relates to coupling one or more adaptors or one or more types of adaptors to one or more target nucleic acids, such as small RNAs. Various methods of coupling various adaptors are provided that minimize or prevent the formation of adaptor-dimers or adaptor-multimers, where such adaptor-dimers or adaptor-multimers can interfere with subsequent processing steps and can present performance issues with nucleic acid library formation and sequencing thereof. Ways to form and use various adaptor-coupled nucleic acids are provided along with various configurations of adaptors, adaptor-coupled nucleic acids, and libraries formed thereof.

In certain embodiments, a method of coupling adaptors to a target nucleic acid is provided. The method can include coupling a first adaptor to a first end of the target nucleic acid to form a coupled first adaptor. A portion of a second adaptor can be hybridized to a portion of the coupled first adaptor to form a hybridized second adaptor, where the hybridized second adaptor includes a single-stranded 3'-end. The hybridized second adaptor can be coupled to a second end of the target nucleic acid to form an adaptor-flanked product, where the adaptor-flanked product includes at least a part of the first adaptor coupled to the first end of the target nucleic acid and at least a part of the second adaptor coupled to the second end of the target nucleic acid. The coupling between the hybridized second adaptor and the second end of the target nucleic acid can be through a pseudo-intramolecular interaction, e.g., as mediated by a suitable enzyme, such as a ligase, e.g., as described below.

Each adaptor can independently include a nucleic acid or a nucleic acid analogue. The adaptor can be formed of ribonucleic acids, deoxyribonucleic acids, or both. Various modified nucleotides can be included in the adaptor, such as nucleotides with modified bases, nucleotides with nonnatural bases, labeled nucleotides, nucleotides modified with various linkers, and nucleotides conjugated with various chemical moieties, including fluorophores, quenchers, solid supports, and antigenic compounds. The adaptor can have one or more labile bases that can be degraded and/or result in strand scission; e.g., deoxy-uracil can be degraded using uracil-DNA glycosylase (UDG) and the abasic site cleaved by subsequent hydrolysis. The adaptor can have various terminal modifications, including having a phosphorylated or a dephosphorylated 5'-end, the presence or absence of a 3'-end hydroxyl, and can include various terminal blocking groups that prevent modification of the respective terminus by one or more enzyme activities or chemical modifications. For example, the blocking group can prevent ligation at the blocked terminus, polymerase extension at the blocked terminus, or exonuclease activity at the blocked terminus. The adaptor can also be formed of a single molecule or can be formed of multiple associated molecules, where the associated molecules are not covalently bonded to each other. For example, multiple oligonucleotides can be hybridized together to form an adaptor or one or more oligonucleotides can be associated with other molecules through various non-covalent interactions. Adaptors that may be added to a target nucleic acid via methods of the invention include, but are not limited to, those described in U.S. application Ser. No. 14/478,978 published as US 2015/0111789, the disclosure of which is herein incorporated by reference.

The target nucleic acid can be single-stranded or double-stranded and can include DNA, RNA, or both. The target nucleic acid can be derived from natural or synthetic sources. For example, the target nucleic acid can be derived from a single cell, a tissue, an organ, or an organism. Various processing steps can be applied to the target nucleic acid prior to the coupling of adaptors thereto. Examples of processing of the target nucleic acid include one or more steps involving purification, fragmentation, size-selection, RNase treatment, DNase treatment, denaturation, hybridization or annealing, labeling, reverse transcription, amplification. In one embodiment, the target nucleic acid includes genomic DNA. In another embodiment, the target nucleic acid includes small RNAs. Further examples of such processing steps include those described in U.S. application Ser. No. 14/478,978 published as US 2015/0111789, the disclosure of which is herein incorporated by reference.

In certain embodiments, the first adaptor can include an adenylated 5'-end and a blocked 3'-end. Coupling the first adaptor to the first end of the target nucleic acid can include ligating the adenylated 5'-end of the first adaptor to a 3'-end of the target nucleic acid including a hydroxyl group. The second adaptor can be configured to hybridize to the first adaptor so that a 5'-end of the first adaptor is double-stranded. The hybridized second adaptor can include a blocked 5'-end and the single-stranded 3'-end of the hybridized second adaptor can include a hydroxyl group. Coupling the hybridized second adaptor to the second end of the target nucleic acid can include ligating the single-stranded 3'-end including the hydroxyl group of the second adaptor to a 5'-end of the target nucleic acid including a phosphate group.

Ligation of the first adaptor and/or the second adaptor to the target nucleic acid can include the use of a ligase. The ligase can include DNA ligase and single-strand DNA ligase, RNA ligase, and single-strand RNA ligase. Examples of RNA ligases include T4 RNA ligase 1, truncated T4 RNA ligase 2, T4 RNA ligase 2 truncated K227Q, T4 RNA ligase 2 truncated KQ, and mutant versions thereof. Where the first adaptor includes an adenylated 5'-end, truncated T4 RNA ligase 2, or a mutant form thereof, can be used to ligate the 5'-end of the first adaptor to a 3'-end of the target nucleic acid including a hydroxyl group. Where the second adaptor includes a single-stranded 3'-end having a hydroxyl group, T4 RNA ligase 1 can be used to ligate the hydroxyl group to a 5'-end of the target nucleic acid including a phosphate group.

In certain embodiments, the method of coupling adaptors to a target nucleic acid can further include synthesizing a complementary nucleic acid strand to the target nucleic acid of the adaptor-flanked product. For example, where the target nucleic acid includes RNA, a complementary nucleic acid strand can be synthesized by reverse transcription using an RNA-dependent DNA polymerase, and where the target nucleic acid includes DNA, a complementary nucleic acid strand can be synthesized by primer extension using a DNA-dependent DNA polymerase. The RNA-dependent DNA polymerase can include a reverse transcriptase, such as a retroviral reverse transcriptase and recombinant or modified forms thereof. The DNA-dependent DNA polymerase can include various prokaryotic or eukaryotic DNA polymerases and recombinant or modified forms thereof. Examples of suitable polymerases and reaction conditions for synthesizing complementary nucleic acids include, but are not limited to, those described in U.S. application Ser. No. 14/478,978 published as US 2015/0111789, the disclosure of which is herein incorporated by reference.

In certain embodiments, the method of coupling adaptors to a target nucleic acid can further include amplifying the complementary nucleic acid strand using at least one amplification primer. The at least one amplification primer can be configured to hybridize to the complementary nucleic acid strand. Amplification can include performing a polymerase chain reaction using a first amplification primer including a 3'-end configured to hybridize to a 3' region of the complementary nucleic acid strand and a second amplification primer including a 3'-end including a sequence from a 5' region of the complementary nucleic acid strand. It is also possible to combine synthesizing a complementary nucleic acid strand to the target nucleic acid of the adaptor-flanked product and amplifying the complementary nucleic acid strand using at least one amplification primer by performing a reverse transcription polymerase chain reaction (RT-PCR). At least one of the first amplification primer and the second amplification primer can also include a barcode. The barcode can include a unique sequence that can serve to identify a particular amplification product. Barcodes can include defined sequences or can include randomized sequences. The first amplification primer and the second amplification primer can include different barcodes. In this manner, the origin of a particular amplification product can be identified and tracked following sequencing of the amplification product. Identification and tracking can further facilitate multiplexing applications using such amplified products, including amplified products from one or more libraries derived from one or more sources of target nucleic acid. Examples of primers and amplifications conditions that may be employed include, but are not limited to, those described in U.S. application Ser. No. 14/478,978 published as US 2015/0111789, the disclosure of which is herein incorporated by reference.

The method of coupling adaptors to a target nucleic acid can also include where the hybridized second adaptor comprises a bridging oligonucleotide and a ligation oligonucleotide. The bridging oligonucleotide can include the portion of the second adaptor that hybridizes to the portion of the coupled first adaptor to form the hybridized second adaptor. The bridging oligonucleotide can also include another portion that hybridizes with a portion of the ligation oligonucleotide, where the ligation oligonucleotide can include the single-stranded 3'-end. The bridging oligonucleotide can include a blocked 5'-end, the ligation oligonucleotide can include a blocked 5'-end, and the single-stranded 3'-end of the ligation nucleotide can include a hydroxyl group. The single-stranded 3'-end of the ligation oligonucleotide can include a hydroxyl group. In this way, coupling the hybridized second adaptor to the second end of the target nucleic acid can include ligating the single-stranded 3'-end of the ligation oligonucleotide including the hydroxyl group to a 5'-end of the target nucleic acid including a phosphate group.

The method of coupling adaptors to a target nucleic acid can further include where the hybridized second adaptor has at least one cleavable site between the portion of the second adaptor that hybridizes to the portion of the coupled first adaptor and another portion of the second adaptor that includes the single-stranded 3'-end. The hybridized second adaptor can also comprise DNA, the at least one cleavable site can include uracil, the hybridized second adaptor can include a blocked 5'-end, and the single-stranded 3'-end of the hybridized second adaptor can include a hydroxyl group. The single-stranded 3'-end of the hybridized second adaptor can include a hydroxyl group. In this way, coupling the hybridized second adaptor to the second end of the target nucleic acid can include ligating the single-stranded 3'-end of the hybridized second adaptor including the hydroxyl group to a 5'-end of the target nucleic acid including a phosphate group. The method can then further include cleaving the at least one cleavable site after coupling the hybridized second adaptor to the second end of the target nucleic acid. The cleaving can therefore result in the portion of the second adaptor that hybridizes to the portion of the coupled first adaptor to thereby include an extendible 3'-end. The cleaving can further result in the another portion of the second adaptor that includes the single stranded 3'-end being coupled to the second end of the target nucleic acid. The extendible 3'-end can thereafter be extended to synthesize a complementary nucleic acid strand. Extension can include the use of one or more polymerases, including a DNA-dependent DNA polymerase and/or an RNA-dependent DNA polymerase. For example, where the target nucleic acid is RNA, the extension can be performed with reverse transcriptase and dNTPs to synthesize a complementary DNA strand. Additional cleavable sites and conditions for cleaving the same that may be employed embodiments of the invention include, but are not limited to, those described in international application serial no. PCT/US2017/036583 (such as chemical and light labile moieties), the disclosure of which is herein incorporated by reference.

The method of coupling adaptors to a target nucleic acid can additionally include where the hybridized second adaptor has a 5' to 5' reverse linker positioned between a portion of the second adaptor and the single-stranded 3'-end of the second adaptor. For example, the 5' to 5' reverse linker can be positioned between the portion of the second adaptor that hybridizes to the portion of the coupled first adaptor and the single-stranded 3'-end of the second adaptor. The single-stranded 3'-end of the hybridized second adaptor can include a first hydroxyl group. In this way, coupling the hybridized second adaptor to the second end of the target nucleic acid can include ligating the single-stranded 3'-end of the hybridized second adaptor including the first hydroxyl group to a 5'-end of the target nucleic acid including a phosphate group. Ligation of the phosphate group and the hydroxyl group forms a ligation site covalently joining the coupled first adaptor and the second adaptor.

The 5' to 5' reverse linker allows the second adaptor to have a 5' to 3' orientation extending in each direction therefrom. As such, the second adaptor can have another 3' end in addition to the single-stranded 3'-end, where the another 3' end can include a second hydroxyl group. The first hydroxyl group and the second hydroxyl group can prevent the second adaptor from self-ligating through either an intermolecular interaction or an intramolecular interaction. The method can then further include extending the another 3' end of the hybridized second adaptor to form an extension product including a complementary nucleic acid strand. The second hydroxyl group at the 3' end of the second adaptor can be extended from the portion of the second adaptor that is hybridized to the portion of the coupled first adaptor. Extension can include the use of one or more polymerases. The extension product therefore includes complementary sequence to the target nucleic acid flanked by a portion complementary to part of the second adaptor and the second adaptor. The extension product also includes the target nucleic acid flanked by at least a part of the first adaptor and at least a part of the second adaptor. Where the target nucleic acid portion of the extension product is RNA, it can be degraded using an RNase, such as RNase H, for example.

The present technology also provides an adaptor-flanked product formed by any one of the methods described herein. A plurality of adaptor-flanked products can be generated from a plurality of target nucleic acids. The plurality of adaptor-flanked products can constitute a library for subsequent processing steps or analyses, including amplification, sequencing, and various types of qualitative and quantitative analyses. The methods may be employed to generate libraries for subsequent sequencing applications. Sequencing applications that may be performed with libraries prepared according to methods of invention include, but are not limited to, those described in U.S. application Ser. No. 14/478,978 published as US 2015/0111789, the disclosure of which is herein incorporated by reference.

Several benefits and advantages can be attributed to the present technology. One significant advantage is that the various ways for coupling adaptors to one or more target nucleic acids provided herein can significantly reduce or even prevent the undesired formation of adaptor-dimers or adaptor-multimers, which can hinder further processing and analysis of the adaptor-flanked product. The present methods can also be faster and easier to perform than other methods that include one or more additional steps to remove or eliminate adaptor-dimers; e.g., size selection by electrophoretic gel purification. The reduction or prevention of adaptor-dimers can also reduce bias and amplification issues for a library of adaptor-flanked products that are generated as described herein. The pseudo-intramolecular coupling between the hybridized second adaptor and the target nucleic acid can also accelerate the ligation kinetics from a diffusion-dependent intermolecular interaction to a pseudo-intramolecular interaction that can be faster and more efficient. Coupling in this manner can also reduce bias in libraries prepared from a population of target nucleic acids using the present methods. In particular, the present technology can significantly reduce ligation-induced bias in preparation of a library of adaptor-flanked products from a sample of target nucleic acids. These advantages further allow a reduction in the input amount of target nucleic acid compared to other methods. An overall savings in time and cost is thereby achieved.

The present technology can further include a kit of adaptors and reagents necessary to couple the adaptors to one or more target nucleic acids as described herein. For example, the kit can be configured as a library preparation kit adapted to convert total RNA or purified small RNA into reformatted, sequencing ready libraries of adaptor-flanked products for use in various next generation sequencing platforms; e.g., Illumina NGS, Ion Torrent, etc. Small RNA sequencing, in particular, is a powerful tool for discovering and profiling the population of small RNAs in a given sample. Although usually practiced in a lower-throughput manner than many other RNA sequencing applications, likely in part due to high cost, long workflow, and suboptimal performance, small RNA sequencing is widely used. There is also emerging interest in using circulating microRNAs as a biomarkers for liquid biopsies. Cancer, cardiovascular disease, infectious disease, stem cells, developmental diseases are also key drivers for microRNA research. The present technology provides improved processes and components for achieving these goals.

A kit for coupling adaptors to a target nucleic acid can include a first adaptor and a second adaptor. The first adaptor can include an adenylated 5'-end and a blocked 3'-end. The second adaptor can include a portion configured to hybridize to a portion of the first adaptor, where the second adaptor can include a single-stranded 3'-end when hybridized to the first adaptor. The second adaptor can be configured to hybridize to the first adaptor so that a 5'-end of the first adaptor is double-stranded. The second adaptor can include a blocked 5'-end and the single-stranded 3'-end of the hybridized second adaptor can include a hydroxyl group.

The kit can include one or more various enzymes and reagents necessary to practice the various methods and steps described herein. For example, the kit can include one or more ligases, polymerases, and reagents, such as truncated T4 RNA ligase 2, or a mutant form thereof, T4 RNA ligase 1 and ATP, an RNA-dependent DNA polymerase, and dNTPs. Amplification reagents can also be included, such as reagents used in reverse-transcription and the polymerase chain reaction, such as thermostable polymerases, buffers, dNTPs, etc. One or more amplification primers can be included that have a 3'-end configured to hybridize to at least a portion of the first adaptor, a portion of a complement of the first adaptor, a portion of the second adaptor, and/or a portion of a complement of the second adaptor. One or more of the amplification primers can include a barcode.

In certain embodiments, the kit can be configured so that the second adaptor includes a bridging oligonucleotide and a ligation oligonucleotide. The bridging oligonucleotide can include the portion of the second adaptor that hybridizes to the portion of the first adaptor. The bridging oligonucleotide can include another portion that hybridizes with a portion of the ligation oligonucleotide. The ligation oligonucleotide can include the single-stranded 3'-end. The bridging oligonucleotide can include a blocked 5'-end, the ligation oligonucleotide can include a blocked 5'-end, and the single-stranded 3'-end of the ligation nucleotide can include a hydroxyl group. The single-stranded 3'-end of the ligation oligonucleotide can include a hydroxyl group.

In certain embodiments, the kit can be configured so that the second adaptor includes at least one cleavable site between the portion of the second adaptor that hybridizes to the portion of the first adaptor and another portion of the second adaptor that includes the single-stranded 3'-end. The second adaptor can include DNA, the at least one cleavable site can include uracil, the second adaptor can include a blocked 5'-end, and the single-stranded 3'-end of the second adaptor can include a hydroxyl group. The single-stranded 3'-end of the second adaptor can include a hydroxyl group. The kit can further include an uracil-DNA glycosylase and/or an apurinic/apyrimidinic (AP) endonuclease.

In certain embodiments, the kit can be configured so that the second adaptor includes a 5' to 5' reverse linker. The 5' to 5' reverse linker can be disposed between the portion of the second adaptor that hybridizes to the portion of the first adaptor and another portion of the second adaptor that includes the single-stranded 3'-end. The single-stranded 3'-end of the second adaptor can include a first hydroxyl group. The second adaptor can include another 3' end, where the another 3' end can include a second hydroxyl group.

In addition to the above-mentioned components, a subject kit may further include instructions for using the components of the kit, e.g., to practice the subject methods as described above. The instructions are generally recorded on a suitable recording medium. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Example embodiments of the present technology are described below in reference to the accompanying figures.

Figure 1:
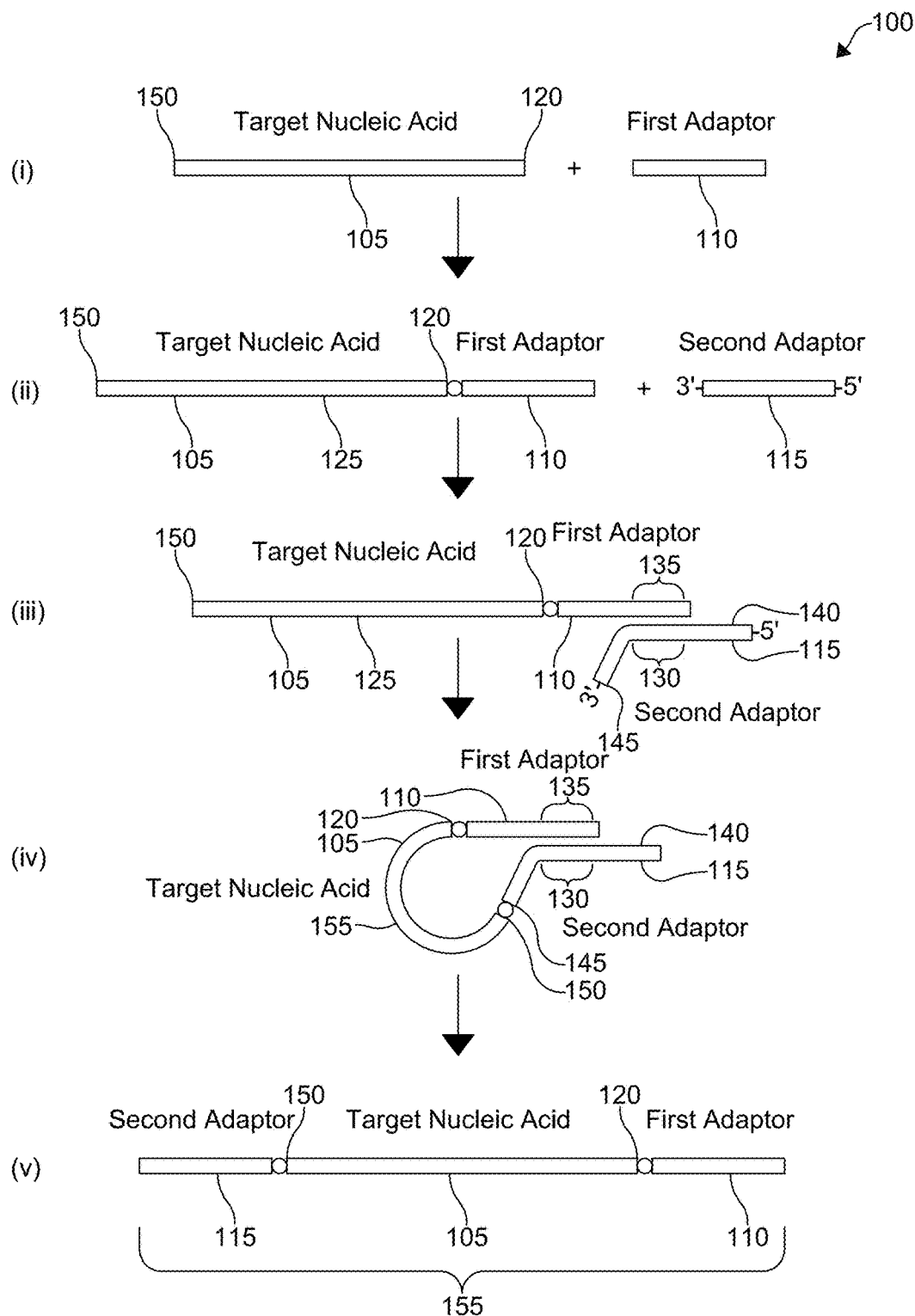
FIG. 1 illustrates a method of coupling adaptors to a target nucleic acid according to a first embodiment of the present technology.

With respect to FIG. 1, a flowchart for a first embodiment of a method 100 of coupling adaptors to a target nucleic acid 105 is shown. For ease of reference, the method 100 is shown divided into steps (i)-(v), however, it is understood that aspects of certain steps can occur concomitantly with each other or in a different order and the method 100 is not limited to the particular sequential presentation depicted in FIG. 1. The flowchart, moreover, only depicts a single target nucleic acid 105, a single first adaptor 110, and a single second adaptor 115, but it is understood that a plurality of target nucleic acids 105, a plurality of first adaptors 110, and a plurality of second adaptors 115 can be employed, including homogenous or heterogeneous populations of each.

Step (i) shows the combination of the target nucleic acid 105 with the first adaptor 110. The first adaptor 110 is coupled to a first end 120 of the target nucleic acid 105 to form a coupled first adaptor 125, as shown in step (ii). For example, the first adaptor 110 can be coupled to the first end 120 of the target nucleic acid 105 by using a ligase. Step (ii) also shows the combination of the coupled first adaptor 125 and the second adaptor 115. As shown, the second adaptor 115 is depicted as a single molecule, however, the second adaptor 115 can include multiple molecules associated in various ways; e.g., the second adaptor 115 can be formed of two or more oligonucleotides that are at least partially hybridized together.

A portion 130 of the second adaptor 115 is hybridized to a portion 135 of the coupled first adaptor 125 in step (iii) to form a hybridized second adaptor 140, where the hybridized second adaptor 140 includes a single-stranded 3'-end 145.

In step (iv), the hybridized second adaptor 140 is coupled to a second end 150 of the target nucleic acid 105 to form an adaptor-flanked product 155. The adaptor-flanked product 155 includes at least a part of the first adaptor 135 coupled to the first end 120 of the target nucleic acid 105 and at least a part of the second adaptor 115 coupled to the second end 150 of the target nucleic acid 105. As shown, formation of the adaptor-flanked product 155 is through a pseudo-intramolecular coupling event. The single stranded 3'-end 145 of the hybridized second adaptor 140 can be coupled to the second end 150 of the target nucleic acid 105 by using a ligase, for example.

Step (v) shows a linear representation of the adaptor-flanked product 155, where the first adaptor 110 is coupled to the first end 120 of the target nucleic acid 105 and the second adaptor 115 is coupled to the second end 150 of the target nucleic acid. Although not depicted, it is understood that one or more sequences of the first adaptor 110 and/or one or more sequences of the second adaptor 115 can be configured to hybridize one or more various primers for primer extension, reverse transcription, and/or amplification steps. These sequences of the first and/or second adaptors 110, 115 can likewise further include a barcode and/or the various primers used for primer extension, reverse transcription, and/or amplification steps can include a barcode.

Figure 2A:
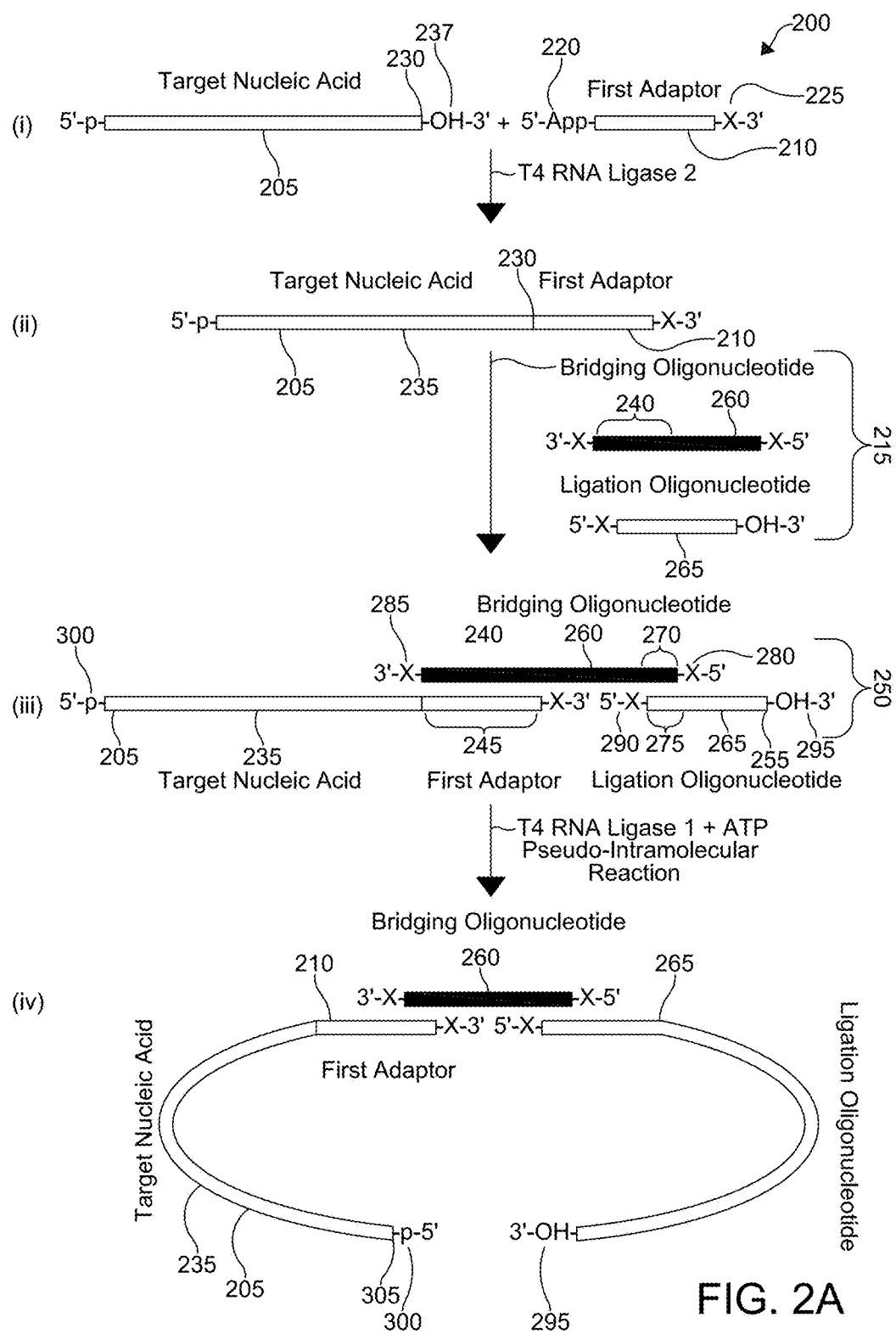
FIG. 2A-2B illustrate a method of coupling adaptors to a target nucleic acid according to a second embodiment of the present technology.
Figure 2B:
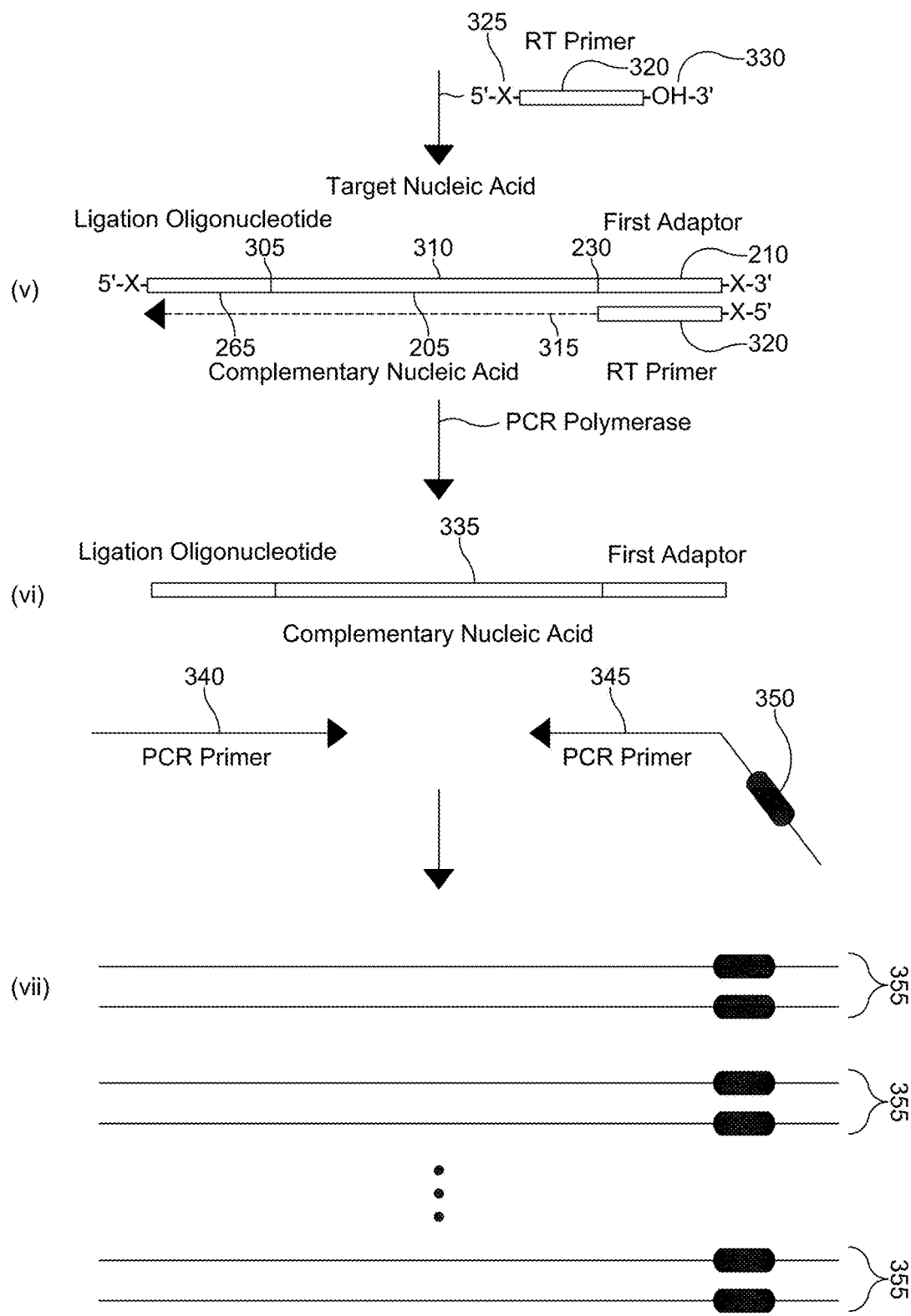

With respect to FIGS. 2A-2B, a flowchart for a second embodiment of a method 200 of coupling adaptors to a target nucleic acid 205 is shown. For ease of reference, the method 200 is shown divided into steps (i)-(vii), however, it is understood that aspects of certain steps can occur concomitantly with each other or in a different order and the method 200 is not limited to the particular sequential presentation depicted in FIGS. 2A-2B. The flowchart, moreover, only depicts a single target nucleic acid 205, a single first adaptor 210, and a single second adaptor 215, but it is understood that a plurality of target nucleic acids 205, a plurality of first adaptors 210, and a plurality of second adaptors 215 can be employed, including homogenous or heterogeneous populations of each.

Step (i) shows the combination of the target nucleic acid 205 with the first adaptor 210. The first adaptor 210 includes an adenylated 5'-end 220 and a blocked 3'-end 225, where the blocked 3'-end 225 chemically protects the first adaptor 210 from enzymatic extension and/or ligation to prevent concatamer formation or circularization. The first adaptor 210 is coupled to a first end 230 of the target nucleic acid 205 to form a coupled first adaptor 235, as shown in step (ii). Coupling the first adaptor 210 to the first end 230 of the target nucleic acid 205 includes ligating the adenylated 5'-end 220 of the first adaptor 210 to the first end 230 of the target nucleic acid 205, where the first end 230 includes a 3'-end of the target nucleic acid 205 including a hydroxyl group 237.

Where, for example, the target nucleic acid 205 includes RNA or size-selected small RNA (<200 nt), the RNA can be placed in a buffer that supports single-stranded nucleic acid ligation. The adenylated first adaptor 210 and truncated T4 RNA ligase 2, or a mutant form thereof, can be used to ligate the 3'-OH at the first end 230 of the target nucleic acid 205 and the pre-activated (adenylated) 5'-end 220 of the first adaptor 210 in an ATP-free ligation reaction. Ligation can be performed at an appropriate temperature and allowed sufficient time to complete the coupling of the first adaptor 210 to the target nucleic acid 205. For example, where the target nucleic acid 205 includes a sample of small RNAs, the small RNA fraction can include a plurality of regulatory micro-RNA (miRNA) as well as tRNA, small nucleolar RNA, and other RNA species. Such small RNAs can each have a 3'-OH and a 5'-phosphate.

The coupled first adaptor 235 can then be combined with the second adaptor 215 and hybridized thereto, as shown in steps (ii) and (iii). In particular, a portion 240 of the second adaptor 215 is hybridized to a portion 245 of the coupled first adaptor 235 to form a hybridized second adaptor 250. The hybridized second adaptor 250 includes a single-stranded 3'-end 255. The hybridized second adaptor 250 comprises a bridging oligonucleotide 260 and a ligation oligonucleotide 265, where the bridging oligonucleotide 260 includes the portion 240 of the second adaptor 215 that hybridizes to the portion 245 of the coupled first adaptor 235 to form the hybridized second adaptor 250. The bridging oligonucleotide 260 includes another portion 270 that hybridizes with a portion 275 of the ligation oligonucleotide 265. The bridging oligonucleotide 260 can be formed of DNA and/or RNA nucleotides and can include modified nucleotides, base analogues, or other chemical modifications. For example, the bridging oligonucleotide 260 can include one or more labile bases that can be degraded; e.g., deoxy-uracil can be degraded using uracil-DNA glycosylase (UDG) and subsequent hydrolysis. The bridging oligonucleotide 260 includes a blocked 5'-end 280 and a blocked 3'-end 285 and the ligation oligonucleotide 265 includes a blocked 5'-end 290 to prevent enzymatic extension and/or the formation of ligation byproducts. The ligation oligonucleotide 265 includes the single-stranded 3'-end 255 of the hybridized second adaptor 250, where the single-stranded 3'-end 255 includes a hydroxyl group 295.

The coupled first adaptor 235, the bridging oligonucleotide 260, and the ligation oligonucleotide 265 can be combined and heat denatured, where the temperature is then lowered to allow hybridization of the respective portions thereof. This can bring the single-stranded 3'-end 255 of the hybridized second adaptor 250 in proximity to the 5'-end of the coupled first adaptor 235 by a pseudo-intramolecular interaction, as shown in step (iv), where the 5'-end of the coupled first adaptor 235 can include a phosphate group 300. While not wishing to be bound by theory, it is believed that this pseudo-intramolecular interaction significantly facilitates coupling of the hydroxyl group 295 at the single-stranded 3'-end 255 of the hybridized second adaptor 250 to the phosphate group 300 at the 5'-end of the coupled first adaptor 235. Coupling in this manner can accelerate the ligation kinetics from a diffusion-dependent intermolecular interaction to a pseudo-intramolecular interaction that can be faster and more efficient. It is further believed that coupling in this manner plays a part in the reduced bias observed in libraries prepared from a population of target nucleic acids 205 using the present methods.

To prevent the undesired formation of dimers and/or concatamer byproducts, the portion 240 of the bridging oligonucleotide 260 that hybridizes to the portion 245 of the coupled first adaptor 235 can hybridize at the former 5'-end of the first adaptor 210, where the first adaptor 210 was coupled to the target nucleic acid 205 to form the coupled first adaptor 235. In this manner, the blocked 3'-end 285 of the bridging oligonucleotide 260 can be flush with the adenylated 5'-end 220 of any hybridized residual first adaptor 210 that was not coupled to the first end 230 of the target nucleic acid 205 in steps (i)-(ii). The blocked 3'-end 285 of the bridging oligonucleotide 260 can also include an overhang that is not complementary and does not hybridize to the former 5'-end of the first adaptor 210. In this manner, the overhanging blocked 3'-end 285 of the bridging oligonucleotide 260 can result in a recessed adenylated 5'-end 220 of any hybridized residual first adaptor 210 that was not coupled to the first end 230 of the target nucleic acid 205 in steps (i)-(ii). These configurations can therefore reduce or prevent any residual first adaptor 210 from reacting with other components and forming undesired byproducts; e.g., undesired ligation between any residual first adaptor 210 and the ligation oligonucleotide 265. The amount of bridging oligonucleotide 260 used in the method 200 can also be greater than the amount of first adaptor 210 used in the method 200 in order to hybridize and reduce or prevent any residual first adaptor 210 from steps (i)-(ii) from reacting with other components.

As shown in steps (iv)-(v), the hybridized second adaptor 250 is coupled to a second end 305 of the target nucleic acid 205 to form an adaptor-flanked product 310. In particular, the ligation oligonucleotide 265 includes the single-stranded 3'-end 255 of the hybridized second adaptor 250, where the single-stranded 3'-end 255 includes the hydroxyl group 295 that is ligated to the phosphate group 300 at the 5'-end of the coupled first adaptor 235. Step (v) shows the adaptor-flanked product 310 including at least a part of the first adaptor 210 coupled to the first end 230 of the target nucleic acid 205 and at least a part of the second adaptor 205 (i.e., the ligation oligonucleotide 265) coupled to the second end 305 of the target nucleic acid 205. A single-strand RNA ligase (e.g., T4 RNA ligase 1) and ATP can be used to ligate the hydroxyl group 295 at the single-stranded 3'-end 255 of the ligation oligonucleotide 265 to the phosphate group 300 at the 5'-end of the coupled first adaptor 235, which are brought together in close proximity by the bridging oligonucleotide 260. Sufficient time is allowed for pseudo-intramolecular ligation to complete. Thus, ligation does not occur at the site of the hybridized bridging oligonucleotide 260, but rather at the distal, non-hybridized ends of the resulting hybridized construct shown in step (iv). The adapter-flanked product 310 can thereafter be made single-stranded or linearized by degrading the bridging oligonucleotide 260 and/or by heat denaturation.

Step (v) shows the synthesis of a complementary nucleic acid strand 315 to the target nucleic acid 205 of the adaptor-flanked product 310. As shown, the complementary nucleic acid strand 315 is extended to include a complement of the ligation oligonucleotide 265. Where the target nucleic acid 205 includes RNA, the synthesis of the complementary nucleic acid strand 315 includes reverse transcription of the RNA, where a reverse transcription (RT) primer 320 can be hybridized to the first adaptor 210 portion of the adaptor-flanked product 310. As shown, the RT primer 320 includes a blocking group 325 at a 5'-end and a hydroxyl group 330 at a 3'-end, where the hydroxyl group 330 is extended following addition of reverse transcriptase and dNTPs to form the complementary nucleic acid strand 315.

As shown in step (vi), the complementary nucleic acid 335 includes complementary sequence to the target nucleic acid 205 flanked by complementary sequences to the ligation oligonucleotide 265 and the first adaptor 210. Depending on the configuration of the RT primer 320 and the extent or location of hybridization to the first adaptor 210, the RT primer 320 can include an entire complement of the first adaptor 210, less than an entire complement of the first adaptor 210, or can include additional sequence not found in the first adaptor 210.

Steps (vi)-(vii) show amplification of the complementary nucleic acid 335 using at least one amplification primer, where a first PCR primer 340 and a second PCR primer 345 are shown. The second PCR primer 345 includes a barcode 350. Amplification using the polymerase chain reaction results in multiple double-stranded DNA products 355 constituting reformatted sequences of the target nucleic acids 205. For example, where the starting target nucleic acid 205 included a population of small RNAs, the double-stranded DNA products 355 provide a library thereof that can be readily subjected to various qualitative and quantitative analyses, including sequencing.

The first PCR primer 340 and the second PCR primer 345 can include sequences required for Next Generation Sequencing (NGS), and are complementary to at least a portion of the first adaptor 210 sequence and to at least a portion of the second adaptor sequence 215 (e.g., the ligation oligonucleotide 265) and each can optionally include one or more sample barcodes. The polymerase chain reaction can be performed using a DNA polymerase, dNTPs, and a buffer that supports PCR amplification. The resulting library of double-stranded DNA products 355 can be amplified to a level suitable for clonal amplification and NGS.

Figure 3A:
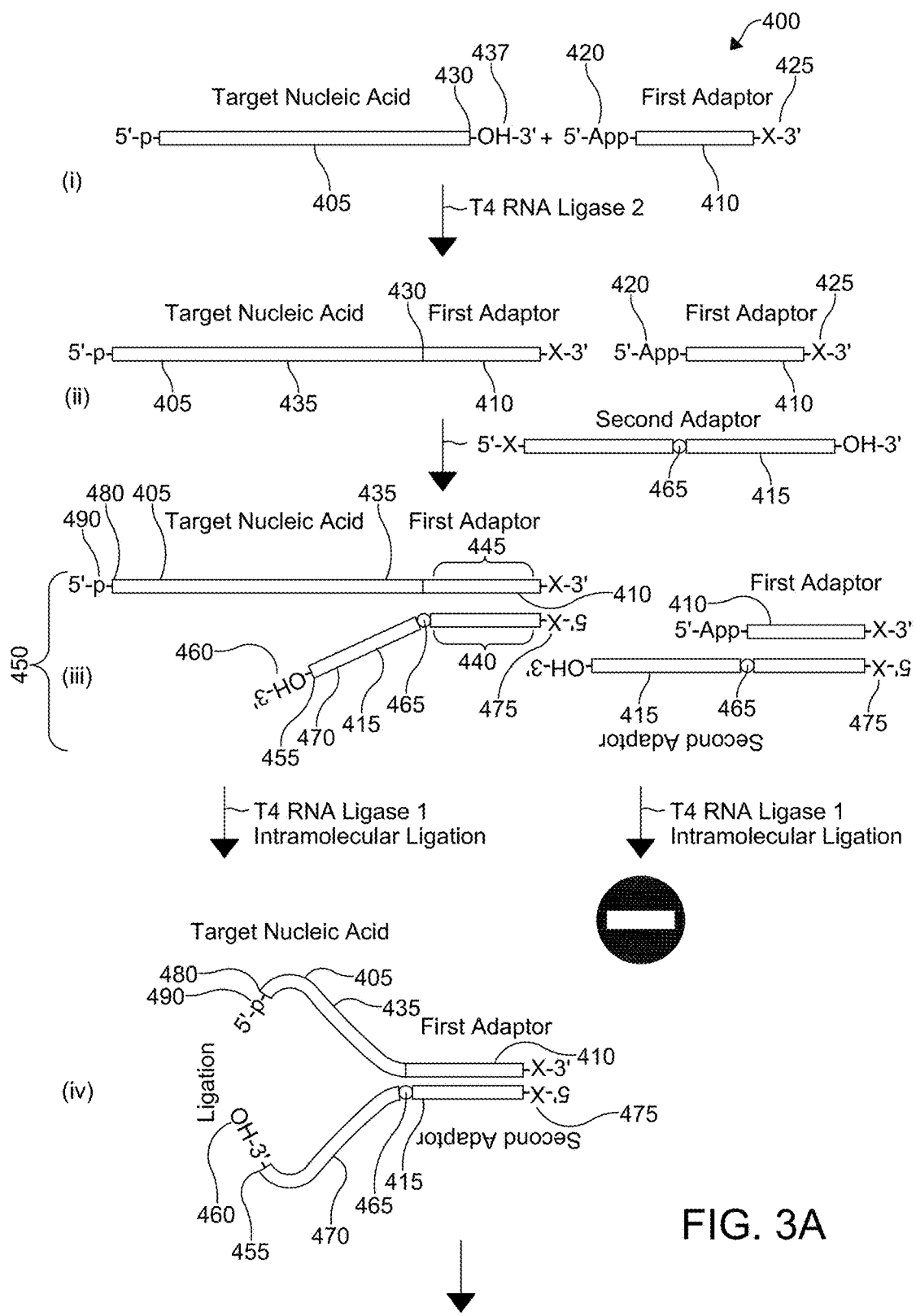
FIG. 3A-3C illustrate a method of coupling adaptors to a target nucleic acid according to a third embodiment of the present technology.
Figure 3B:
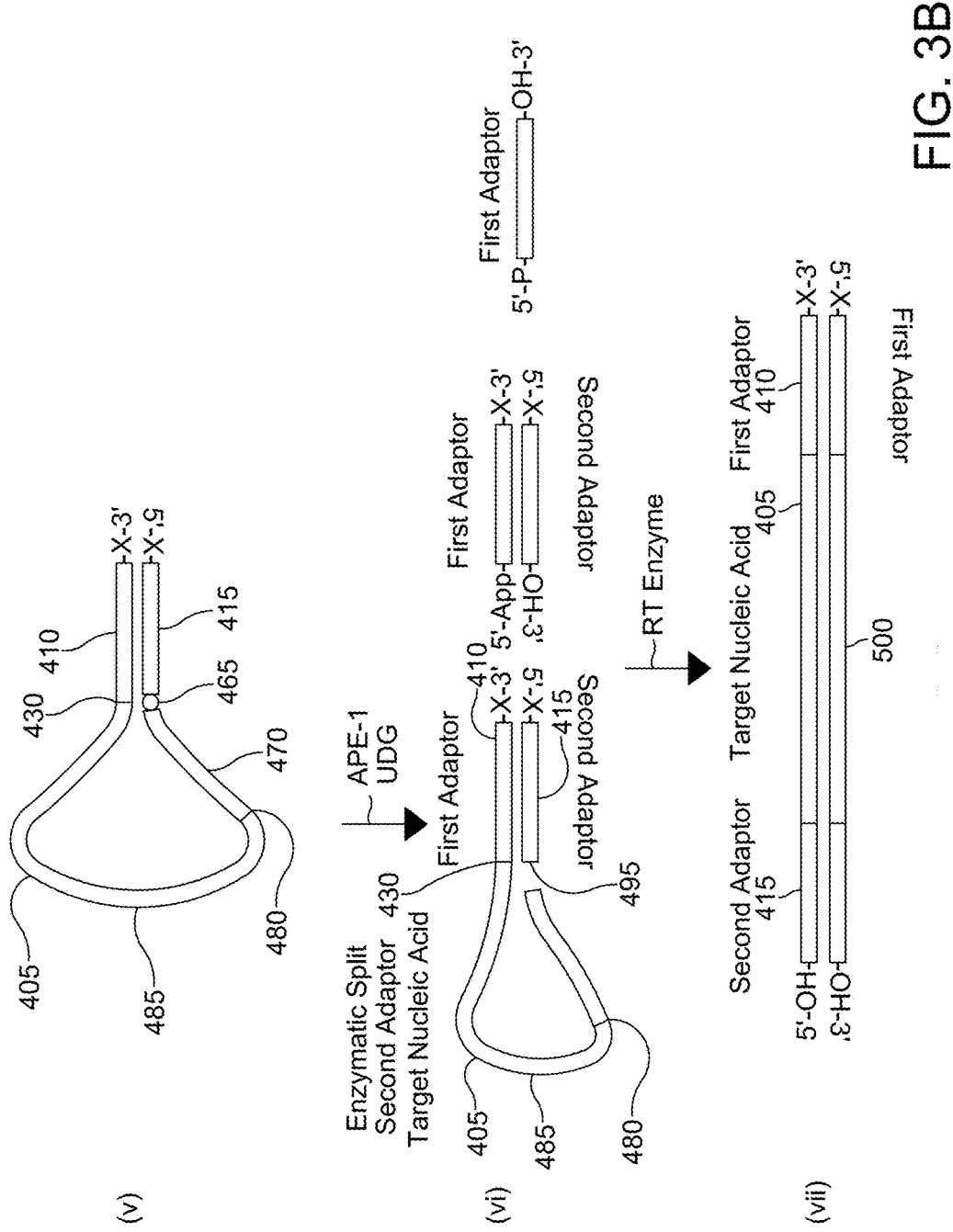
Figure 3C:
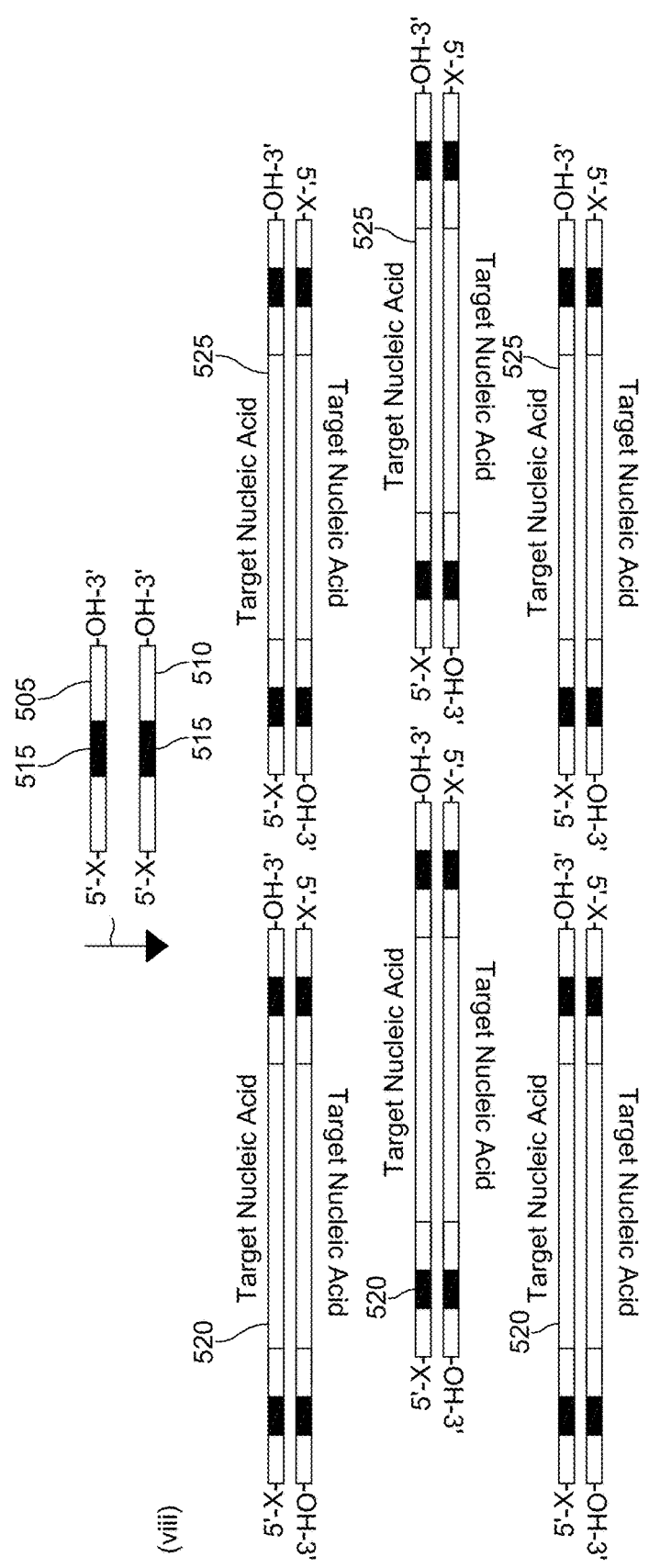
Figure 4A:
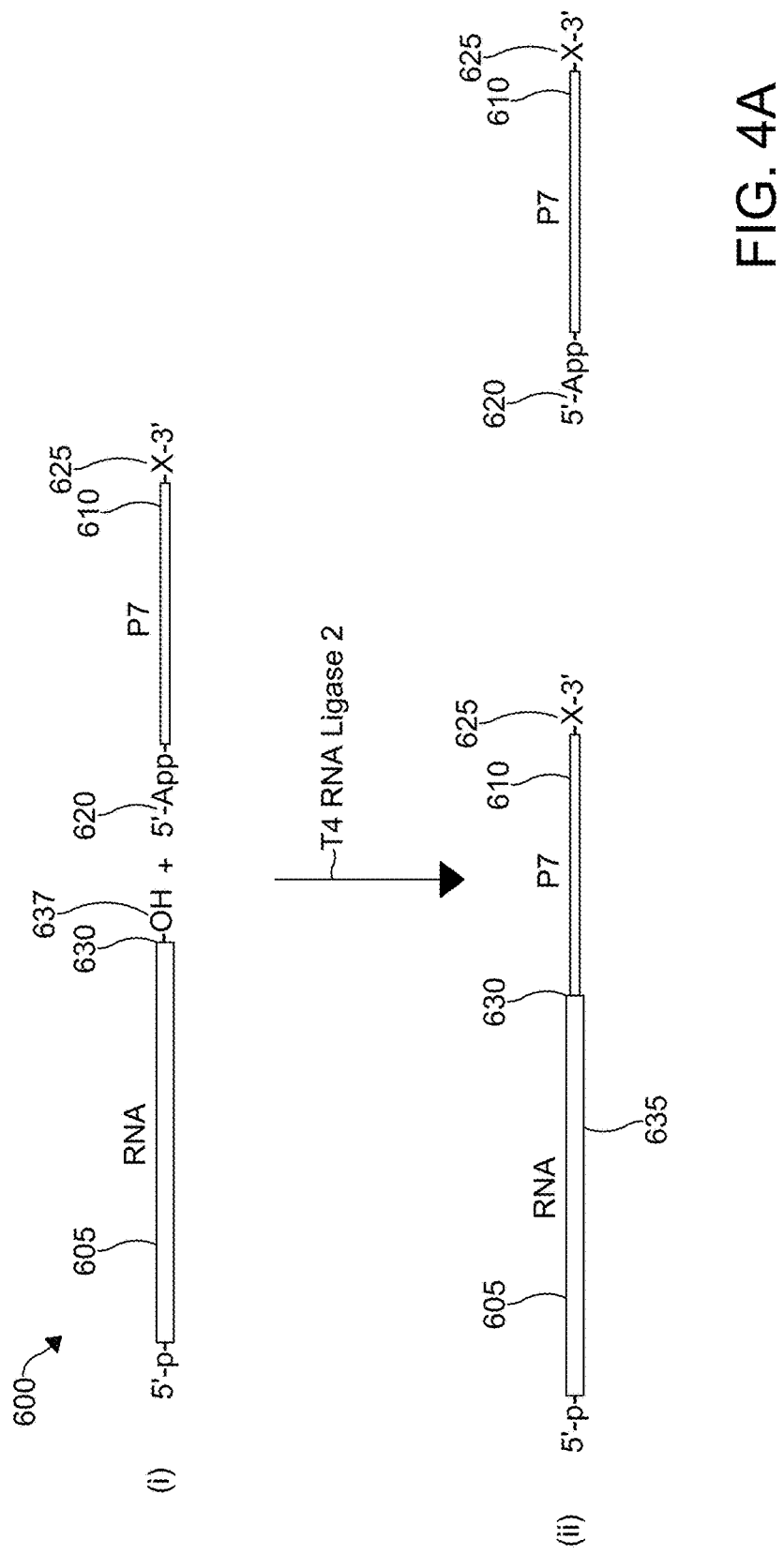
FIG. 4A-4E illustrate a method of coupling adaptors to a target nucleic acid according to a fourth embodiment of the present technology.
Figure 4B:
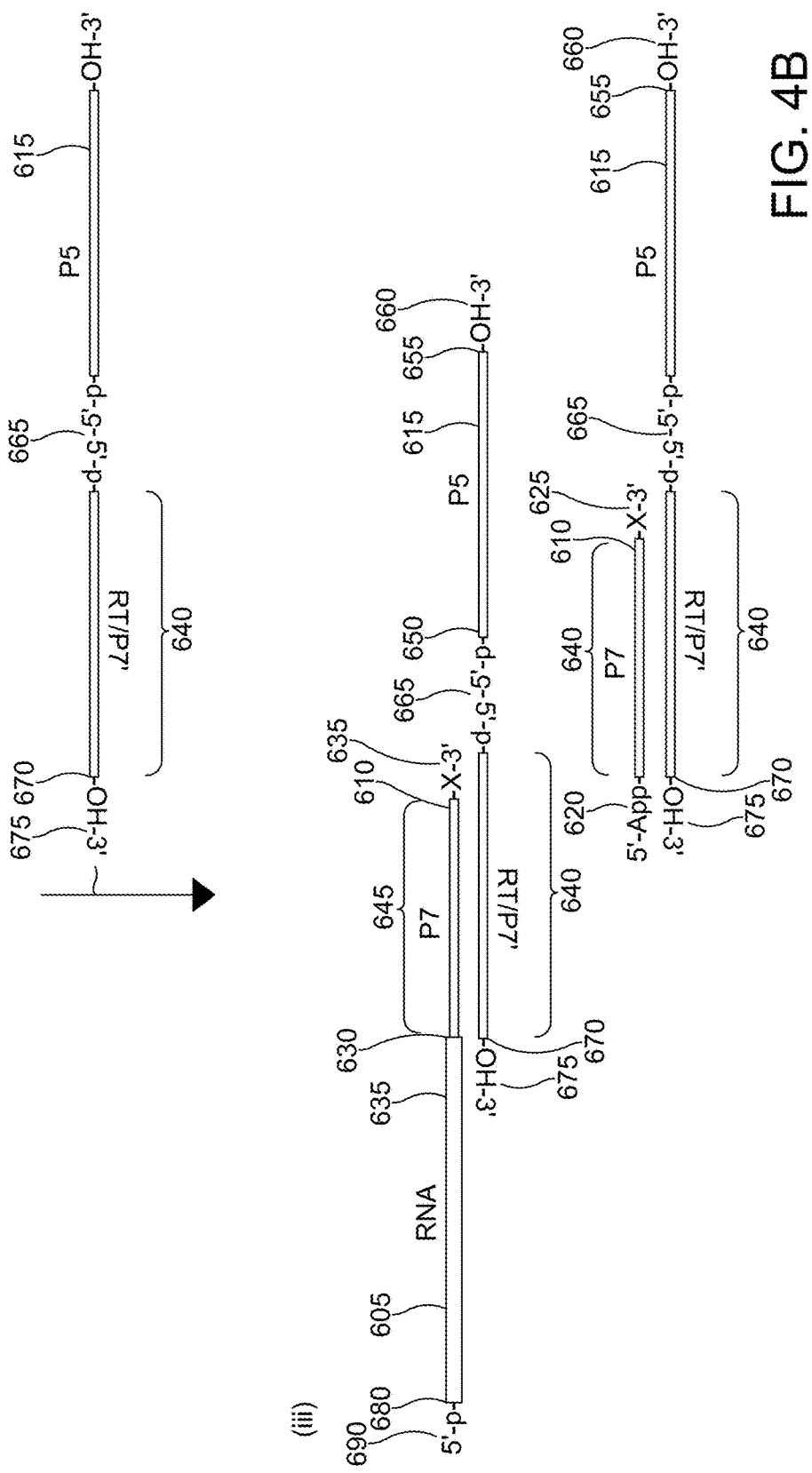
Figure 4C:
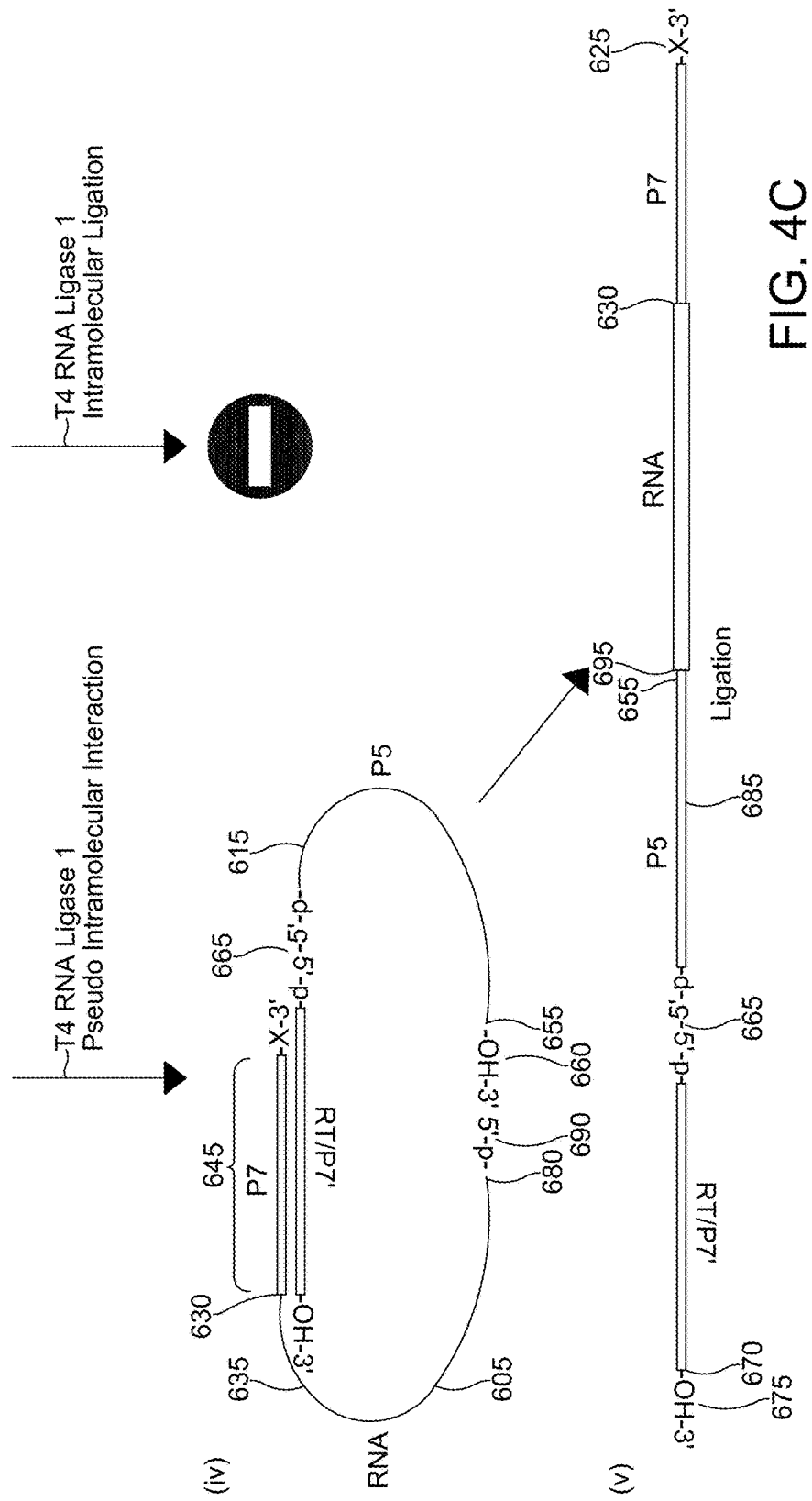
Figure 4D:
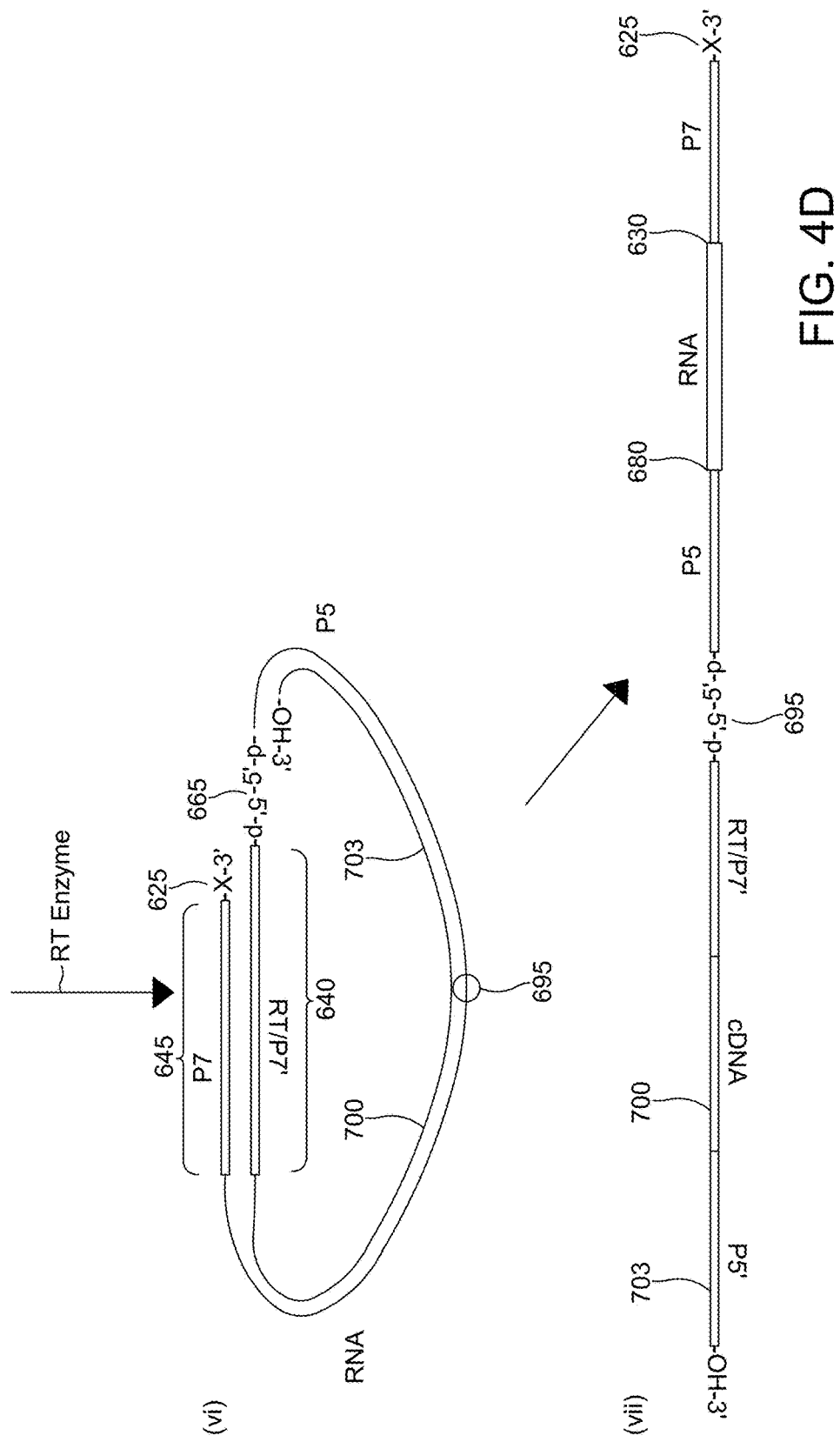
Figure 4E:
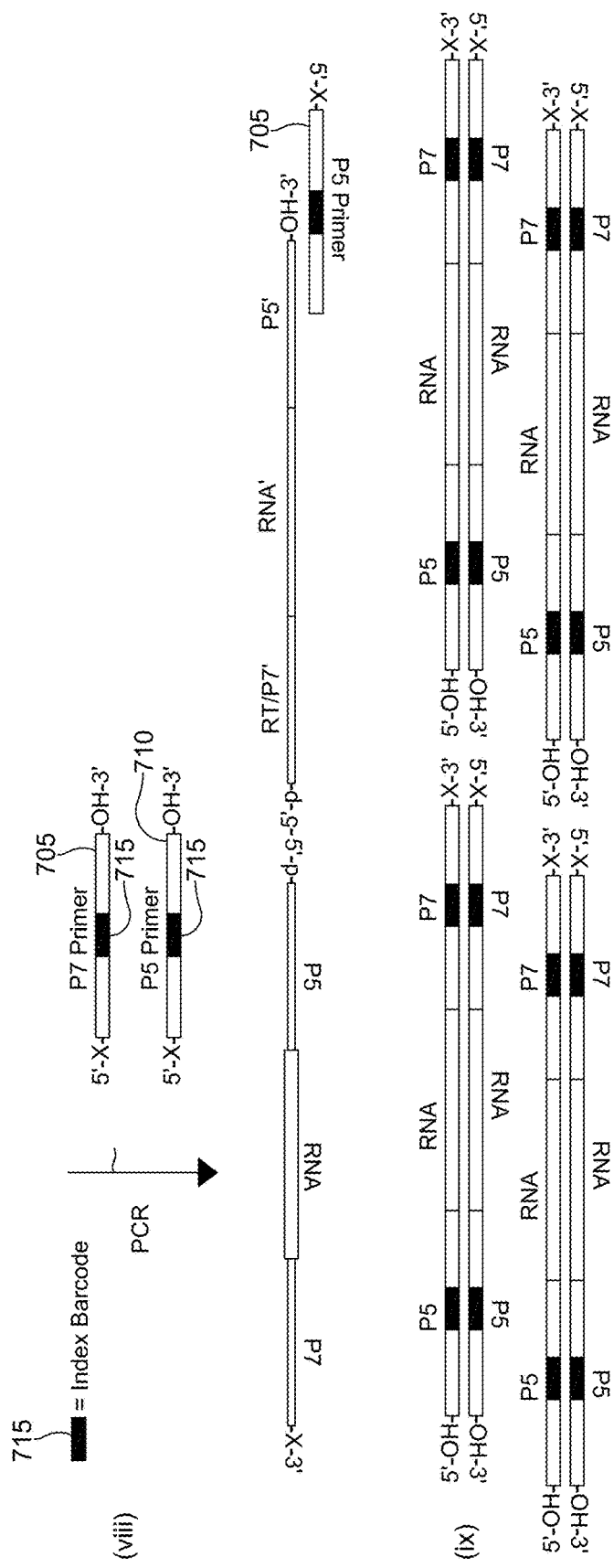

With respect to FIGS. 3A-3C, a flowchart for a third embodiment of a method 400 of coupling adaptors to a target nucleic acid 405 is shown. For ease of reference, the method 400 is shown divided into steps (i)-(viii), however, it is understood that aspects of certain steps can occur concomitantly with each other or in a different order and the method 400 is not limited to the particular sequential presentation depicted in FIGS. 3A-3C. The flowchart, moreover, only depicts a single target nucleic acid 405, a single first adaptor 410, and a single second adaptor 415, but it is understood that a plurality of target nucleic acids 405, a plurality of first adaptors 410, and a plurality of second adaptors 415 can be employed, including homogenous or heterogeneous populations of each.

Step (i) shows the combination of the target nucleic acid 405 with the first adaptor 410. The first adaptor 410 includes an adenylated 5'-end 420 and a blocked 3'-end 425, where the blocked 3'-end 425 chemically protects the first adaptor 410 from enzymatic extension and/or ligation to prevent concatamer formation or circularization. The first adaptor 410 is coupled to a first end 430 of the target nucleic acid 405 to form a coupled first adaptor 435, as shown in step (ii). Coupling the first adaptor 410 to the first end 430 of the target nucleic acid 405 includes ligating the adenylated 5'-end 420 of the first adaptor 410 to the first end 430 of the target nucleic acid 405, where the first end 430 includes a 3'-end of the target nucleic acid 405 including a hydroxyl group 437.

Where, for example, the target nucleic acid 405 includes RNA or size-selected small RNA (<200 nt), aliquots containing 5 ng to 3000 ng of RNA can be placed in a buffer that supports single-stranded RNA ligation. The adenylated first adaptor 410 is combined with truncated T4 RNA ligase 2, or a mutant form thereof, to join the hydroxyl group 437 at the first end 430 of the target nucleic acid 405 and the pre-activated (adenylated) 5'-end 420 of the first adaptor 410 in an ATP-free ligation reaction. Ligation can be carried out for 1-2 hrs at an appropriate temperature. For example, where the target nucleic acid 405 includes a sample of small RNAs, the small RNA fraction can include a plurality of regulatory microRNA (miRNA) as well as tRNA, small nucleolar RNA, and other RNA species. Such small RNAs can each have a 3'-OH and a 5'-phosphate.

The coupled first adaptor 435 can then be combined with the second adaptor 415 and hybridized thereto, as shown in steps (ii) and (iii). For example, the temperature can be increased to heat-inactivate the truncated T4 RNA ligase 2, or a mutant form thereof, used to couple the first adaptor 410 to the first end 430 of the target nucleic acid 405 and to denature the coupled first adaptor 435 of the first coupling reaction. The temperature is then reduced and sufficient time provided to hybridize the coupled first adaptor 435 and the second adaptor 415.

In particular, a portion 440 of the second adaptor 415 is hybridized to a portion 445 of the coupled first adaptor 435 to form a hybridized second adaptor 450. The second adaptor 415, forming part of the hybridized second adaptor 450, includes a single-stranded 3'-end 455, where the single-stranded 3'-end 455 includes a hydroxyl group 460. The second adaptor 415, forming part of the hybridized second adaptor 450, includes at least one cleavable site 465 between the portion 440 of the second adaptor 415 that hybridizes to the portion 445 of the coupled first adaptor 435 and another portion 470 of the second adaptor 415 that includes the single-stranded 3'-end 455. For example, the at least one cleavable site 465 can include a labile base that can be degraded; e.g., deoxy-uracil can be made abasic using uracil-DNA glycosylase (UDG) followed by cleavage using an apurinic/apyrimidinic (AP) endonuclease such as APE-1. As shown in step (iii), the at least one cleavable site 465 can be positioned on the 3' side of the portion 440 of the second adaptor 415 that is hybridized to the portion 445 of the coupled first adaptor 435. The at least one cleavable site 465, however, can also be positioned within the portion 440 of the second adaptor 415 that is hybridized to the portion 445 of the coupled first adaptor 435. The second adaptor 415 includes a blocked 5'-end 475 to prevent enzymatic extension and/or the formation of ligation byproducts. The second adaptor 415 can be formed of DNA and/or RNA nucleotides and can include modified nucleotides, base analogues, or other chemical modifications in order to optimize hybridization stability (e.g., increase Tm), for example.

Also shown in step (ii) is the presence of excess first adaptor 410 that was not coupled to the target nucleic acid 405 to form the coupled first adaptor 435. Excess second adaptor 415 can hybridize to the excess first adaptor 410, as shown in step (iii), which results in a recessed adenylated 5'-end 420 that can reduce or prevent ligation of the excess first adaptor 410 and minimize undesired byproducts. In this way, for example, excess first adaptor 410 is made inaccessible to T4 RNA ligase 1 added in steps (iii)-(iv), which can ligate single stranded nucleic acids.

Steps (iv)-(v) show coupling of the hybridized second adaptor 450 to a second end 480 of the target nucleic acid 405 to form an adaptor-flanked product 485, the adaptor-flanked product 485 including at least a part of the first adaptor 410 coupled to the first end 430 of the target nucleic acid 405 and at least a part of the second adaptor 415 coupled to the second end 480 of the target nucleic acid 405. In particular, the second end 480 of the target nucleic acid 405 (i.e., the 5'-end of the coupled first adaptor 435, as shown) can include a phosphate group 490 that is ligated to the hydroxyl group 460 at the single-stranded 3'-end 455 of the hybridized second adaptor 450 using T4 RNA ligase 1 and ATP. This pseudo-intramolecular interaction is believed to significantly facilitate coupling of the hydroxyl group 460 at the single-stranded 3'-end 455 of the hybridized second adaptor 450 to the phosphate group 490 at the 5'-end of the coupled first adaptor 435. Coupling in this manner can accelerate the ligation kinetics from a diffusion-dependent intermolecular interaction to a pseudo-intramolecular interaction that can be faster and more efficient. It is further believed that coupling in this manner plays a part in the reduced bias observed in libraries prepared from a population of target nucleic acids 405 using the present methods.

As shown in step (vi), the at least one cleavable site 465 is cleaved after coupling the hybridized second adaptor 450 to the second end 480 of the target nucleic acid 405. The at least one cleavable site 465 can include deoxy-uracil, which can be cleaved by treatment with uracil-DNA glycosylase (UDG) and an apurinic/apyrimidinic (AP) endonuclease, such as APE-1. The cleaving results in the portion 440 of the second adaptor 415 that hybridizes to the portion 455 of the coupled first adaptor 435 to include an extendible 3'-end 495 and the another portion 470 of the second adaptor 415 that formerly included the single stranded 3'-end 455 coupled to the second end 480 of the target nucleic acid 405.

The portion 440 of the second adaptor 415 that hybridizes to the portion 455 of the coupled first adaptor 435, which now includes the extendible 3'-end 495, can function as a primer for a primer extension reaction. The extendible 3'-end 495 can be extended to synthesize a complementary nucleic acid strand 500 to the target nucleic acid 405 of the adaptor-flanked product 485. Where the target nucleic acid 405 includes RNA, synthesis of the complementary nucleic acid strand includes reverse transcription of the RNA by a reverse transcriptase (RT). As shown in step (vii), the complementary nucleic acid 500 includes complementary sequence to the target nucleic acid 405 flanked by a complementary sequence to part of the second adaptor 415 and a complementary sequence to at least part of the first adaptor 410.

Step (viii) shows amplification of the complementary nucleic acid strand 500 using at least one amplification primer, where a first PCR primer 505 and a second PCR primer 510 are shown. The first and second primers 505, 510 can each include a barcode 515. Amplification using the polymerase chain reaction results in multiple double-stranded DNA products 520 constituting reformatted sequences of the target nucleic acids 405. For example, where the starting target nucleic acid 405 included a population of small RNAs, the double-stranded DNA products 520 provide a library thereof that can be readily subjected to various qualitative and quantitative analyses, including sequencing.

The first PCR primer 505 and the second PCR primer 510 can include sequences required for Next Generation Sequencing (NGS), and are complementary to at least a portion of the first adaptor 410 sequence and to at least a portion of the second adaptor sequence 415, respectively, and each can optionally include one or more sample barcodes 515. The polymerase chain reaction can be performed using a DNA polymerase, dNTPs, and a buffer that supports PCR amplification. The resulting library of double-stranded DNA products 520 can be amplified to a level suitable for clonal amplification and NGS.

With respect to FIGS. 4A-4E, a flowchart for a fourth embodiment of a method 600 of coupling adaptors to a target nucleic acid 605 is shown. For ease of reference, the method 600 is shown divided into steps (i)-(ix), however, it is understood that aspects of certain steps can occur concomitantly with each other or in a different order and the method 600 is not limited to the particular sequential presentation depicted in FIGS. 4A-4E. The flowchart, moreover, only depicts a single target nucleic acid 605, a single first adaptor 610, and a single second adaptor 615, but it is understood that a plurality of target nucleic acids 605, a plurality of first adaptors 610, and a plurality of second adaptors 615 can be employed, including homogenous or heterogeneous populations of each.

Step (i) shows the combination of the target nucleic acid 605 with the first adaptor 610. The first adaptor 610 includes an adenylated 5'-end 620 and a blocked 3'-end 625, where the blocked 3'-end 625 chemically protects the first adaptor 610 from enzymatic extension and/or ligation to prevent concatamer formation or circularization. The first adaptor 610 is coupled to a first end 630 of the target nucleic acid 605 to form a coupled first adaptor 635, as shown in step (ii). Coupling the first adaptor 610 to the first end 630 of the target nucleic acid 605 includes ligating the adenylated 5'-end 620 of the first adaptor 610 to the first end 630 of the target nucleic acid 605, where the first end 630 includes a 3'-end of the target nucleic acid 605 including a hydroxyl group 637.

Where, for example, the target nucleic acid 605 includes RNA or size-selected small RNA (<200 nt), aliquots containing 5 ng to 3000 ng of RNA can be placed in a buffer that supports single-stranded RNA ligation. The adenylated first adaptor 610 is combined with truncated T4 RNA ligase 2, or a mutant form thereof, to join the hydroxyl group 637 at the first end 630 of the target nucleic acid 605 and the pre-activated (adenylated) 5'-end 620 of the first adaptor 610 in an ATP-free ligation reaction. Ligation can be carried out for 1-2 hrs at an appropriate temperature. For example, where the target nucleic acid 605 includes a sample of small RNAs, the small RNA fraction can include a plurality of regulatory microRNA (miRNA) as well as tRNA, small nucleolar RNA, and other RNA species. Such small RNAs can each have a 3'-OH and a 5'-phosphate.

The coupled first adaptor 635 can then be combined with the second adaptor 615 and hybridized thereto, as shown in steps (ii) and (iii). For example, the temperature can be increased to heat-inactivate the truncated T4 RNA ligase 2, or a mutant form thereof, used to couple the first adaptor 610 to the first end 630 of the target nucleic acid 605 and to denature the coupled first adaptor 635 of the first coupling reaction. The temperature is then reduced and sufficient time provided to hybridize the coupled first adaptor 635 and the second adaptor 615.

In particular, a portion 640 of the second adaptor 615 is hybridized to a portion 645 of the coupled first adaptor 635 to form a hybridized second adaptor 650. The second adaptor 615, forming part of the hybridized second adaptor 650, includes a single-stranded 3'-end 655, where the single-stranded 3'-end 655 includes a first hydroxyl group 660. The second adaptor 615 includes a 5' to 5' reverse linker 665 positioned between the portion 640 of the second adaptor 615 and the single-stranded 3'-end 655. The 5' to 5' reverse linker 665 allows the second adaptor 615 to have a 5' to 3' orientation extending in each direction therefrom. In this way, the second adaptor 615 can have a 3' end 670 opposite from the single-stranded 3'-end 655, where the 3' end 670 can include a second hydroxyl group 675. Accordingly, the first hydroxyl group 660 and the second hydroxyl group 675 prevent the second adaptor 615 from self-ligating through either an intermolecular interaction or an intramolecular interaction. The second adaptor 615 can be formed of DNA and/or RNA nucleotides and can include modified nucleotides, base analogues, or other chemical modifications in order to optimize hybridization stability (e.g., increase Tm), for example. The second adaptor 615 can also include one or more can labile bases that can be degraded; e.g., deoxyuracil can be made abasic using uracil-DNA glycosylase (UDG) followed by cleavage using an apurinic/apyrimidinic (AP) endonuclease such as APE-1.

Also shown in step (ii) is the presence of excess first adaptor 610 that was not coupled to the target nucleic acid 605 to form the coupled first adaptor 635. Excess second adaptor 615 can hybridize to the excess first adaptor 610, as shown in step (iii), which can result in a recessed or blunt adenylated 5'-end 620 that can reduce or prevent ligation of the excess first adaptor 610 and minimize undesired byproducts. In this way, for example, excess first adaptor 610 is made inaccessible to T4 RNA ligase 1 added in steps (iii)-(v), which can ligate single stranded nucleic acids.

Steps (iv)-(v) show coupling of the hybridized second adaptor 650 to a second end 680 of the target nucleic acid 605 to form an adaptor-flanked product 685, the adaptor-flanked product 685 including at least a part of the first adaptor 610 coupled to the first end 630 of the target nucleic acid 605 and at least a part of the second adaptor 615 coupled to the second end 680 of the target nucleic acid 605. In particular, the second end 680 of the target nucleic acid 605 (i.e., the 5'-end of the coupled first adaptor 635, as shown) can include a phosphate group 690 that is ligated to the hydroxyl group 660 at the single-stranded 3'-end 655 of the hybridized second adaptor 650 using T4 RNA ligase 1 and ATP. This pseudo-intramolecular interaction is believed to significantly facilitate coupling of the hydroxyl group 660 at the single-stranded 3'-end 655 of the hybridized second adaptor 650 to the phosphate group 690 at the 5'-end of the coupled first adaptor 635. Ligation of the phosphate group 690 and the hydroxyl group 660 forms a ligation site 695 covalently joining the coupled first adaptor 635 and the second adaptor 615. Coupling in this manner can accelerate the ligation kinetics from a diffusion-dependent intermolecular interaction to a pseudo-intramolecular interaction that can be faster and more efficient. It is further believed that coupling in this manner plays a part in the reduced bias observed in libraries prepared from a population of target nucleic acids 605 using the present methods.

As shown in step (vi), an extension reaction is performed post-coupling of the hybridized second adaptor 650 to the second end 680 of the target nucleic acid 605 to form an extension product 700. The second hydroxyl group 675 at the 3' end 670 of the second adaptor 615 can be extended from the portion 640 of the second adaptor 615 that is hybridized to the portion 645 of the coupled first adaptor 635. Extension can include the use of one or more polymerases, including a DNA-dependent DNA polymerase and/or an RNA-dependent DNA polymerase. For example, where the target nucleic acid 605 is RNA, the extension can be performed with reverse transcriptase and dNTPs to synthesize a complementary DNA strand to the target nucleic acid 605, through the ligation site 695 of the phosphate group 690 and the hydroxyl group 660, ending at or near the 5' to 5' reverse linker 665. The spiral-like depiction of the extension product 700 in step (vi) illustrates the extension reaction, where the extension product 700 is shown in linear form for clarity in step (vii). Heat can be used to denature the self-complementarity of the extension product 700. The resulting extension product 700 therefore includes complementary sequence to the target nucleic acid 605 flanked by a portion 703 complementary to part of the second adaptor 615 and the second adaptor 615. The extension product 695 also includes the target nucleic acid 605 flanked by at least a part of the first adaptor 610 and at least a part of the second adaptor 615. Where the target nucleic acid 605 portion of the extension product 695 is RNA, it can be degraded using an RNase, such as RNase H, for example (not shown).

Steps (viii)-(ix) show amplification of the extension product 700 using at least one amplification primer, where a first PCR primer 705 and a second PCR primer 710 are shown. The first and second primers 705, 710 can each include a barcode 715. Where the target nucleic acid 605 includes RNA and is maintained as part of the extension product 700, the amplification can include reverse transcription. Amplification using the polymerase chain reaction results in multiple double-stranded DNA products 720 constituting reformatted sequences of the target nucleic acids 605. For example, where the starting target nucleic acid 605 included a population of small RNAs, the double-stranded DNA products 720 provide a library thereof that can be readily subjected to various qualitative and quantitative analyses, including sequencing.

The first PCR primer 705 and the second PCR primer 710 can include sequences required for Next Generation Sequencing (NGS), and can include sequences comprising at least a portion of the first adaptor 610 sequence (or a complement thereof) and the second adaptor sequence 415 (or a complement thereof), respectively, and each can optionally include one or more sample barcodes 715. The polymerase chain reaction can be performed using a DNA polymerase, dNTPs, and a buffer that supports PCR amplification. The resulting library of double-stranded DNA products 720 can be amplified to a level suitable for clonal amplification and NGS.

The following examples are offered by way of illustration and not by way of limitation.

EXPERIMENTAL

Adaptor Modification of Target miRNA
A. Materials and Methods
The protocol illustrated in FIGS. 2A and 2B is employed to add adaptors to target miRNA molecules for subsequent amplification, as described in greater detail below:
a. 3' adapter ligation: An—RNA sample is obtained from cells or tissues via column purification or phenol-chloroform extraction and Ethanol precipitation. The obtained RNA sample has miRNA molecules with 5'-phosphate and 3'-hydroxyl modifications. The miRNA molecules are ligated at the 3' end to an adapter that is pre-adenylated at the 5' end and blocked at the 3'-end, e.g., as illustrated in FIG. 2A, steps (i) and (ii). The sequence of the adaptor is 5'-rAPP-TGGAATTCTCGGGTGCCAAGG-3' (SEQ ID NO:01) (Illumina TruSeq Small RNA kit (RA3). Ligation occurs via the action of T4 RNA Ligase 2, truncated (K227Q), at 25° C. for 1-2 hours.
b. Splint oligo hybridization: A Splint oligo, blocked at the 5'- and 3'-ends, and partially complementary to the 3' and 5' adapter sequences, is hybridized to the 3'-ligated adapter. Examples of Splint oligos that are employed include:

```
                                       (SEQ ID NO: 02)
Biotin-ACTGTAGAACTCTGAACAAACACCCGAGAATTCCANNN-C3

(SEQ ID NO: 03)
Biotin-ACUGUAGAACUCUGAACAAACACCCGAGAAUUCCANNN-C3

(SEQ ID NO: 04)
AmC6-ACTGTAGAACTCTGAACAAACACCCGAGAATTCCANNN-C3

(SEQ ID NO: 05)
AmC6-ACUGUAGAACUCUGAACAAACACCCGAGAAUUCCANNN-C3

(SEQ ID NO: 06)
AmC6-CCTTGGCACCCGAGAATTCCA-U-GTTCAGAGTTCTACAGTCCGA
CGATC (SEQ ID NO: 07)
AmC6-CC TTG GCA CCC GAGAAUUCC A-GT TCA GAG TTC TAC
AGT CCG ACG ATC (SEQ ID NO: 08)
AmC6-CC/ideoxyU/ /ideoxyU/GG CAC CCG AGA A/
ideoxyU//ideoxyU/CCA GTT CAG AGT TCT ACA GTC CGA
CGA TC (SEQ ID NO: 09)
Biotin-CCTTGGCACCCGAGAATTCCA-U-GTTCAGAGTTCTACAGTCC
GACGATC (SEQ ID NO: 10)
Biotin-CC TTG GCA CCC GAGAAUUCC A-GT TCA GAG TTC
TAC AGT CCG ACG ATC (SEQ ID NO: 11)
/5Biosg/CC/ideoxyU/ /ideoxyU/GG CAC CCG AGA A/
ideoxyU//ideoxyU/CCA GTT CAG AGT TCT ACA GTC CGA
CGA TC
```

The 5'-adapter, blocked at the 5'-end, is then added to the reaction and incubated with all oligos and ligated RNA. The sequence of the 5'-adaptor is:
5'-GUUCAGAGUUCUACAGUCCGACGAUC-3' (SEQ ID NO:012) (Illumina TruSeq Small RNA kit (RA5)) The Splint oligo brings the 5'-adapter and RNA ligated to the 3'-adapter in close proximity, as illustrated in FIG. 2A, step (iii) (it is noted that the Splint oligo is referred to as the Bridging Oligonucleotide, and the 5'-adaptor is referred to as the Ligation Oligonucleotide).
c. 5' adapter ligation: A pseudo-intramolecular circularization reaction occurs with the 5'-adapter in close proximity to the RNA of interest using T4 RNA Ligase 1 for 1-2 hours at 25° C., e.g. as shown in FIG. 2A, step (iv).
d. RT oligo hybridization: An RT oligo, blocked at the 5'-end and complementary to the 3'adapter sequence, is hybridized to the adapter, e.g., as shown in FIG. 2B, step (v). The sequence of the adapter is: 5'-GCCTTGGCACCCGA-GAATTCCA-3' (SEQ ID NO:13)(Illumina TruSeq Small RNA kit (RA5)).
e. Reverse Transcription: Reverse transcriptase (SuperScript II from Invitrogen) and nucleotides are added to the reaction, which is maintained at 42° C. for 15-30 minutes.
f. PCR: Barcoded primers and a universal primer are added to the samples alongside nucleotides, buffer and a polymerase (which was one of KAPA 2GR, KAPA HiFi, NEB Taq, NEB LongAmp Taq, and Takara SeqAmp), e.g., as shown in FIG. 2B, step (vi).
The universal primer sequence is:

```
                                       (SEQ ID NO: 14)
5'-AATGATACGGCGACCACCGAGATCTACACGTTCAGAGTTCTACAGTC
CGA
```

-continued

The barcoded primers have the sequence:

(SEQ ID NO: 15)
5'-CAAGCAGAAGACGGCATACGAGATNNNNNNGTGACTGGAGTTCCTTG
GCACCCGAGAATTCCA

In the above sequence, the barcode is labeled as NNNNNN and the constant domain is not underlined.
The samples are amplified according to the following parameters:
94° C. for 30 sec followed by
10-20 reps of:
94° C. 30 sec, 62° C. 20 sec, 72° C. for 10 sec
One last extension at 65° C. for 10 min
g. PCR product purification and size-selection: PCR products are purified via column and run on a Pippin prep instrument or on PAGE to select for material migrating around 140-150 bp in size.
h. Sequencing: Size-selected material is sequenced.
B. Results
The results are shown in FIG. 5. FIG. 5 provides a graphical illustration showing the percentage of miRNA enriched at least 2-fold. Using the protocol illustrated in FIGS. 2A and 2B, 65% of the miRNA in the initial sample is enriched 2-fold or greater.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A method of coupling adaptors to a target nucleic acid, the method comprising:
   coupling a first adaptor to a first end of the target nucleic acid to form a coupled first adaptor;
   hybridizing a portion of a second adaptor to a portion of the coupled first adaptor to produce a hybridized structure having a hybridized second adaptor in which the hybridized second adaptor comprises a single-stranded 3'-end; and
   coupling the single-stranded 3'-end of the hybridized second adaptor of the hybridized structure to a second end of the target nucleic acid to form an adaptor-flanked product, the adaptor-flanked product comprising at least a part of the first adaptor coupled to the first end of the target nucleic acid and at least a part of the second adaptor coupled to the second end of the target nucleic acid.

2. The method of claim 1, wherein the first adaptor comprises an adenylated 5'-end and a blocked 3'-end, and coupling the first adaptor to the first end of the target nucleic acid comprises ligating the adenylated 5'-end of the first adaptor to a 3'-end of the target nucleic acid comprising a hydroxyl group.

3. The method of claim 1, wherein the second adaptor is configured to hybridize to the first adaptor so that a 5'-end of the first adaptor is double-stranded.

4. The method of claim 1, wherein the hybridized second adaptor comprises a blocked 5'-end and the single-stranded 3'-end of the hybridized second adaptor comprises a hydroxyl group.

5. The method of claim 4, wherein coupling the hybridized second adaptor to the second end of the target nucleic acid comprises ligating the single-stranded 3'-end comprising the hydroxyl group of the second adaptor to a 5'-end of the target nucleic acid including a phosphate group.

6. The method of claim 1, further comprising synthesizing a complementary nucleic acid strand to the target nucleic acid of the adaptor-flanked product.

7. The method of claim 6, wherein the target nucleic acid comprises RNA and synthesizing a complementary nucleic acid strand comprises reverse transcription of the RNA.

8. The method of claim 6, further comprising amplifying the complementary nucleic acid strand using at least one amplification primer, the at least one amplification primer configured to hybridize to the complementary nucleic acid strand.

9. The method of claim 8, wherein amplifying the complementary nucleic acid strand using at least one amplification primer comprises performing a polymerase chain reaction using a first amplification primer comprising a 3'-end configured to hybridize to a 3' region of the complementary nucleic acid strand and a second amplification primer comprising a 3'-end able to hybridize to a sequence from a 5' region of the complementary nucleic acid strand.

10. The method of claim 9, wherein at least one of the first amplification primer and the second amplification primer comprises a barcode.

11. The method of claim 1, wherein the hybridized second adaptor comprises a bridging oligonucleotide and a ligation oligonucleotide, the bridging oligonucleotide being the part of the second adaptor that hybridizes to the portion of the coupled first adaptor to form the hybridized second adaptor and comprising another portion that hybridizes with a portion of the ligation oligonucleotide, the ligation oligonucleotide comprising the single-stranded 3'-end.

12. The method of claim 11, wherein the bridging oligonucleotide comprises a blocked 5'-end, the ligation oligonucleotide comprises a blocked 5'-end, and the single-stranded 3'-end of the ligation nucleotide comprises a hydroxyl group.

13. The method of claim 11, wherein the single-stranded 3'-end of the ligation oligonucleotide comprises a hydroxyl group and coupling the hybridized second adaptor to the second end of the target nucleic acid comprises ligating the single-stranded 3'-end of the ligation oligonucleotide comprising the hydroxyl group to a 5'-end of the target nucleic acid comprising a phosphate group.

14. The method of claim 1, wherein the hybridized second adaptor comprises at least one cleavable site between the portion of the second adaptor that hybridizes to the portion of the coupled first adaptor and another portion of the second adaptor that comprises the single-stranded 3'-end.

15. The method of claim 14, wherein the hybridized second adaptor comprises DNA, the at least one cleavable site comprises uracil, the hybridized second adaptor comprises a blocked 5'-end, and the single-stranded 3'-end of the hybridized second adaptor comprises a hydroxyl group.

16. The method of claim 11, wherein the single-stranded 3'-end of the hybridized second adaptor comprises a hydroxyl group and coupling the hybridized second adaptor to the second end of the target nucleic acid comprises ligating the single-stranded 3'-end of the hybridized second adaptor comprising the hydroxyl group to a 5'-end of the target nucleic acid comprising a phosphate group.

17. The method of claim 14, further comprising cleaving the at least one cleavable site after coupling the hybridized second adaptor to the second end of the target nucleic acid, the cleaving resulting in the portion of the second adaptor that hybridizes to the portion of the coupled first adaptor to comprise an extendible 3'-end and the another portion of the second adaptor that comprises the single stranded 3'-end coupled to the second end of the target nucleic acid.

18. The method of claim 14, further comprising extending the extendible 3'-end and synthesizing a complementary nucleic acid strand.

19. The method of claim 1, wherein the hybridized second adaptor comprises a 5' to 5' reverse linker.

20. The method of claim 19, wherein the 5' to 5' reverse linker is between the portion of the second adaptor that hybridizes to the portion of the coupled first adaptor and another portion of the second adaptor that comprises the single-stranded 3'-end.

21. The method of claim 19, wherein the single-stranded 3'-end of the hybridized second adaptor comprises a first hydroxyl group and coupling the hybridized second adaptor to the second end of the target nucleic acid comprises ligating the single-stranded 3'-end of the hybridized second adaptor comprising the first hydroxyl group to a 5'-end of the target nucleic acid comprising a phosphate group.

22. The method of claim 19, wherein the second adaptor comprises another 3' end.

23. The method of claim 22, wherein the another 3' end comprises a second hydroxyl group.

24. The method of claim 22, further comprising extending the another 3' end and synthesizing a complementary nucleic acid strand.

25. The method of claim 1, wherein the second adaptor comprises at least four non-random nucleotides at the 5' end.

26. The method of claim 1, wherein the first adaptor is coupled to the 3'-end of the target nucleic acid.

* * * * *

SEQUENCE LISTING

<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<222> LOCATION: (1)..(1)
<223> OTHER INFORMATION: Oligonucleotide is linked to 5',5'-adenyl
    pyrophosphoryl

<400> SEQUENCE: 1
tggaattctc gggtgccaag g                                              21

<210> SEQ ID NO 2
<211> LENGTH: 38
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (1)..(1)
<223> OTHER INFORMATION: Nucleotide is linked to biotin
<220> FEATURE:
<221> NAME/KEY: misc_feature
<222> LOCATION: (36)..(38)
<223> OTHER INFORMATION: n is a, c, g, or t

<400> SEQUENCE: 2
actgtagaac tctgaacaaa cacccgagaa ttccannn                            38

<210> SEQ ID NO 3
<211> LENGTH: 38
<212> TYPE: RNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (1)..(1)
<223> OTHER INFORMATION: Nucleotide is linked to biotin
<220> FEATURE:
<221> NAME/KEY: misc_feature
<222> LOCATION: (36)..(38)

<223> OTHER INFORMATION: n is a, c, g, or u

<400> SEQUENCE: 3
acuguagaac ucugaacaaa cacccgagaa uuccannn                                    38

<210> SEQ ID NO 4
<211> LENGTH: 38
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (1)..(1)
<223> OTHER INFORMATION: Nucleotide is linked to 5'-Amino-Modifier C6
<220> FEATURE:
<221> NAME/KEY: misc_feature
<222> LOCATION: (36)..(38)
<223> OTHER INFORMATION: n is a, c, g, or t

<400> SEQUENCE: 4
actgtagaac tctgaacaaa cacccgagaa ttccannn                                    38

<210> SEQ ID NO 5
<211> LENGTH: 38
<212> TYPE: RNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (1)..(1)
<223> OTHER INFORMATION: Nucleotide is linked to 5'-Amino-Modifier C6
<220> FEATURE:
<221> NAME/KEY: misc_feature
<222> LOCATION: (36)..(38)
<223> OTHER INFORMATION: n is a, c, g, or u

<400> SEQUENCE: 5
acuguagaac ucugaacaaa cacccgagaa uuccannn                                    38

<210> SEQ ID NO 6
<211> LENGTH: 48
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (1)..(1)
<223> OTHER INFORMATION: Nucleotide is linked to 5'-Amino-Modifier C6

<400> SEQUENCE: 6
ccttggcacc cgagaattcc augttcagag ttctacagtc cgacgatc                         48

<210> SEQ ID NO 7
<211> LENGTH: 47
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (1)..(1)
<223> OTHER INFORMATION: Nucleotide is linked to 5'-Amino-Modifier C6

<400> SEQUENCE: 7
ccttggcacc cgagaauucc agttcagagt tctacagtcc gacgatc                          47

```
<210> SEQ ID NO 8
<211> LENGTH: 47
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (1)..(1)
<223> OTHER INFORMATION: Nucleotide is linked to 5'-Amino-Modifier C6
<220> FEATURE:
<221> NAME/KEY: misc_feature
<222> LOCATION: (3)..(4)
<223> OTHER INFORMATION: Nucleotide is deoxy-uracil
<220> FEATURE:
<221> NAME/KEY: misc_feature
<222> LOCATION: (18)..(19)
<223> OTHER INFORMATION: Nucleotide is deoxy-uracil

<400> SEQUENCE: 8
ccuuggcacc cgagaauucc agttcagagt tctacagtcc gacgatc         47

<210> SEQ ID NO 9
<211> LENGTH: 48
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (1)..(1)
<223> OTHER INFORMATION: Nucleotide is linked to biotin

<400> SEQUENCE: 9
ccttggcacc cgagaattcc augttcagag ttctacagtc cgacgatc        48

<210> SEQ ID NO 10
<211> LENGTH: 47
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (1)..(1)
<223> OTHER INFORMATION: Nucleotide is linked to biotin

<400> SEQUENCE: 10
ccttggcacc cgagaauucc agttcagagt tctacagtcc gacgatc         47

<210> SEQ ID NO 11
<211> LENGTH: 47
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (1)..(1)
<223> OTHER INFORMATION: Nucleotide is linked to 5' biotin
<220> FEATURE:
<221> NAME/KEY: misc_feature
<222> LOCATION: (3)..(4)
<223> OTHER INFORMATION: Nucleotide is deoxy-uracil
<220> FEATURE:
<221> NAME/KEY: misc_feature
<222> LOCATION: (18)..(19)
<223> OTHER INFORMATION: Nucleotide is deoxy-uracil

<400> SEQUENCE: 11
ccuuggcacc cgagaauucc agttcagagt tctacagtcc gacgatc         47
```

-continued

```
<210> SEQ ID NO 12
<211> LENGTH: 26
<212> TYPE: DNA
<213> ORGANISM: Artificial sequence
<220> FEATURE:
<223> OTHER INFORMATION: Synthetic nucleotide

<400> SEQUENCE: 12
guucagaguu cuacaguccg acgauc                                          26

<210> SEQ ID NO 13
<211> LENGTH: 22
<212> TYPE: DNA
<213> ORGANISM: Artificial sequence
<220> FEATURE:
<223> OTHER INFORMATION: Synthetic nucleotide

<400> SEQUENCE: 13
gccttggcac ccgagaattc ca                                              22

<210> SEQ ID NO 14
<211> LENGTH: 50
<212> TYPE: DNA
<213> ORGANISM: Artificial sequence
<220> FEATURE:
<223> OTHER INFORMATION: Synthetic nucleotide

<400> SEQUENCE: 14
aatgatacgg cgaccaccga gatctacacg ttcagagttc tacagtccga               50

<210> SEQ ID NO 15
<211> LENGTH: 63
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (25)..(30)
<223> OTHER INFORMATION: n is a, c, g, t or u

<400> SEQUENCE: 15
caagcagaag acggcatacg agatnnnnnn gtgactggag ttccttggca cccgagaatt    60
cca                                                                  63
```